(12) United States Patent
Zou et al.

(10) Patent No.: US 11,534,134 B2
(45) Date of Patent: *Dec. 27, 2022

(54) THREE-DIMENSIONAL ULTRASOUND IMAGING METHOD AND DEVICE

(71) Applicant: SHENZHEN MINDRAY BIO-MEDICAL ELECTRONICS CO., LTD., Shenzhen (CN)

(72) Inventors: Yaoxian Zou, Shenzhen (CN); Muqing Lin, Shenzhen (CN); Zhijie Chen, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 286 days.

This patent is subject to a terminal disclaimer.

(21) Appl. No.: 16/903,221

(22) Filed: Jun. 16, 2020

(65) Prior Publication Data

US 2020/0383659 A1  Dec. 10, 2020

Related U.S. Application Data

(63) Continuation of application No. 15/800,387, filed on Nov. 1, 2017, now Pat. No. 10,702,240, which is a continuation of application No. PCT/CN2015/078494, filed on May 7, 2015.

(51) Int. Cl.
| | |
|---|---|
| *A61B 8/00* | (2006.01) |
| *A61B 8/08* | (2006.01) |
| *A61B 8/14* | (2006.01) |

(52) U.S. Cl.
CPC .......... *A61B 8/0866* (2013.01); *A61B 8/0808* (2013.01); *A61B 8/0816* (2013.01); *A61B 8/14* (2013.01); *A61B 8/466* (2013.01); *A61B 8/483* (2013.01); *A61B 8/523* (2013.01); *A61B 8/5223* (2013.01); *A61B 8/4405* (2013.01); *A61B 8/4427* (2013.01); *A61B 8/4472* (2013.01)

(58) Field of Classification Search
CPC .................................................... A61B 8/0866
See application file for complete search history.

(56) References Cited

U.S. PATENT DOCUMENTS

| | | |
|---|---|---|
| 2007/0287915 A1 | 12/2007 | Akaki |
| 2011/0125016 A1 | 5/2011 | Lazebnik |
| 2011/0224546 A1 | 9/2011 | Lee |
| 2014/0205164 A1 | 7/2014 | Ando |

FOREIGN PATENT DOCUMENTS

| | | |
|---|---|---|
| CN | 101069647 | 11/2007 |
| CN | 104114096 | 10/2014 |
| CN | 104156967 | 11/2014 |
| CN | 104414680 | 3/2015 |
| EP | 2390839 | 11/2011 |
| JP | H04295346 | 10/1992 |

*Primary Examiner* — Joseph M Santos Rodriguez
(74) *Attorney, Agent, or Firm* — Kory D. Christensen

(57) ABSTRACT

The three-dimensional ultrasound imaging method comprise emitting an ultrasonic wave to a fetal head; receiving an ultrasonic echo to acquire an ultrasonic echo signal; acquiring three-dimensional volume data of the fetal head according to the ultrasonic echo signal; detecting a median sagittal section from the three-dimensional volume data according to features of the median sagittal section of the fetal head; determining a facing orientation of the fetal head in the median sagittal section; displaying the median sagittal section as an image suitable for observation according to the facing orientation of the fetal head.

13 Claims, 10 Drawing Sheets

THREE-DIMENSIONAL ULTRASOUND IMAGING METHOD AND DEVICE

CROSS-REFERENCE TO RELATED APPLICATIONS

This application is a continuation of U.S. patent application Ser. No. 15/800,387, filed Nov. 1, 2017, for THREE-DIMENSIONAL ULTRASOUND IMAGING METHOD AND DEVICE, which is a continuation of PCT Application No. PCT/CN2015/078494, filed May 7, 2015, both of which are incorporated herein by reference.

TECHNICAL FIELD

The present disclosure relates to medical ultrasound imaging, and more particularly to a three-dimensional ultrasound imaging method and device.

BACKGROUND

Ultrasound imaging is generally used by doctors to inspect tissues within a human body. A doctor may place the probe on the surface of the skin above the target tissues, after which ultrasound images of the tissue may be obtained. Due to its safety, convenience, non-invasiveness and low cost, ultrasound imaging has become one of the primary tools to aid in medical diagnoses. Obstetrics is one of the fields in which ultrasound imaging is most widely used. With the use of ultrasound, the effects of X-rays and the like on the mother and the fetus may be avoided making it superior to other imaging modalities. With ultrasound imaging, not only may observation and measurement of the fetus in morphology be conducted, but also information about physiology and pathology, such as respiratory and urinary information, may be obtained, thereby evaluating the health and growth status of the fetus.

When inspecting the nervous system of the fetus, the corpus callosum and the cerebellar vermis are two very important inspection targets. The corpus callosum is the largest conjugate fiber between the hemispheres of the brain, and is responsible for the communication between the cerebral hemispheres. Deficiency or hypogenesis of the corpus callosum will lead to several complications, such as epilepsy, mental retardation or dyskinesia. Deficiency or hypogenesis of the cerebellar vermis is a symptom of Dandy-Walker syndrome. Fifty percent of patients with the Dandy-Walker syndrome show signs mental retardation and usually have chromosome abnormalities and other deformities with poor prognoses and high mortality rates. Accordingly, the abnormalities of the corpus callosum and the cerebellar vermis represent critical diseases. If they are not found during the prenatal examination, they could bring huge mental and economic burdens to the family of the patient and the society. However, the corpus callosum and the cerebellar vermis are very easy to be misdiagnosed or missed during the inspection of the nervous system of the fetus. The reason is that it is very difficult to obtain the median sagittal section image of the fetus, which is the best image for observing the corpus callosum and the cerebellar vermis, by a conventional two-dimensional ultrasound imaging due to the affects of the factors such as fetal position, amniotic fluid, obstruction of the nasal bone, and skill of the doctors, etc. Even if the image of the median sagittal section can be obtained, doing so may take a long time. Accordingly, many doctors have to indirectly inspect the corpus callosum and the cerebellar vermis by images of other sections (such as the cerebellum section or the thalamus section, etc.), increasing the risk of misdiagnosis.

Recently, with the widespread use of the three-dimensional ultrasound imaging, some doctors perform a three-dimensional scanning on the fetus starting from the biparietal diameter section, obtain an image of the median sagittal section of the fetus by geometric transforms of 3D ultrasound image data, such as manual rotation and translation, and then inspect the corpus callosum and the cerebellar vermis through this median sagittal section image. Although the median sagittal section image obtained by this method may have relatively lower quality than a conventional two-dimensional image, the corpus callosum and the cerebellar vermis can be relatively clearly displayed, and abnormalities of the corpus callosum and the cerebellar vermis can be determined quickly and precisely. In order to image the median sagittal section in three-dimensional space by manual rotation and translation, the doctors must understand the three-dimensional space very well. However, most doctors have no science and engineering background and lack the requisite understanding of three-dimensional space. Therefore it is very difficult for doctors to obtain the median sagittal section image from volume data.

SUMMARY

In one embodiment, a three-dimensional ultrasound imaging method and device are provided, which can three-dimensionally image the fetal head, automatically extract the median sagittal section image of the fetal head, determine the orientation of the fetal head, and adjust the median sagittal section image based on the determined orientation such that the median sagittal section image is suitable for human observation.

The technical solutions provided by the embodiments of the present disclosure may include the following. In one embodiment, a three-dimensional ultrasound imaging method is provided. The method may include transmitting ultrasound waves to a fetal head; receiving ultrasound echoes to obtain ultrasound echo signals; obtaining three-dimensional volume data of the fetal head using the ultrasound echo signals; extracting a median sagittal section image from the three-dimensional volume data based on characteristics of a median sagittal section of a fetal head; detecting image regions representing specific tissue areas of the fetal head in the median sagittal section image and/or in a section image which is parallel to or intersects with the median sagittal section image; determining an orientation of the fetal head in the median sagittal section image based on the image regions; and rotating the median sagittal section image based on the orientation of the fetal head such that in the rotated median sagittal section image the feta head is in a pre-set orientation, or marking the orientation of the fetal head in the median sagittal section image.

In one embodiment, a three-dimensional ultrasound imaging device is provided. The device may include a probe which transmits ultrasound waves to a fetal head and receives ultrasound echoes to obtain ultrasound echo signals; a three-dimensional imaging unit which obtains three-dimensional volume data of the fetal head using the ultrasound echo signals, extracts a median sagittal section image from the three-dimensional volume data based on characteristics of a median sagittal section of a fetal head, determines an orientation of the fetal head in the median sagittal section image, and rotates the median sagittal section image based on the orientation of the fetal head such that in the rotated median sagittal section image the fetal head is in a pre-set orientation or marks the orientation of the fetal head in the median sagittal section image; and a display which display the median sagittal section image.

In the embodiments of the present disclosure, ultrasound scanning may be performed on the fetus to obtain the three-dimensional volume data of the fetal head, and the median sagittal section image of the fetal head may be automatically extracted according to the obtained three-dimensional volume data. Thereafter, the orientation of the fetal head in the median sagittal section image may be automatically determined (e.g., determining whether the fetus is upside down and which side the face is towards), and the median sagittal section image may be adjusted based on the results of the determination such that the displayed median sagittal section image will be suitable for human observation. Accordingly, the doctor can more easily identify and observe the median sagittal section image of the fetal head.

BRIEF DESCRIPTION OF THE DRAWINGS

In order to describe the technical solutions of the embodiments more clearly, the drawing to be used in the description of the embodiment will be briefly described, where the same reference number represents the same part.

DETAILED DESCRIPTION

Figure 1:
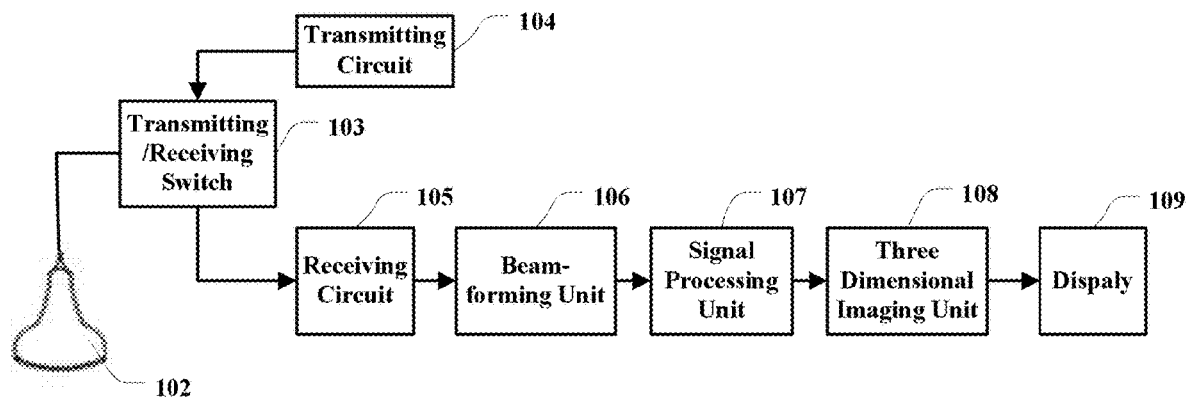
FIG. 1 is a schematic block diagram of a three-dimensional ultrasound imaging device in one embodiment.

In one embodiment, a three-dimensional ultrasound imaging device may be provided. A block diagram of the device is shown in FIG. 1. The three-dimensional ultrasound imaging device may include a probe 102, a transmitting/receiving switch 103, a transmitting circuit 104, a receiving circuit 105, a beam-forming unit 106, a signal processing unit 107, a three-dimensional imaging unit 108 and a display 109. The transmitting circuit 104 may transmit a group of pulses which have been focused by delay to the probe 102 to excite the probe 102 transmit ultrasound beams to the tissue to be examined (no shown in the figure). After a certain time, the probe 102 may receive the ultrasound echoes which are reflected by the tissue and carry the information related to the tissue, and convert the ultrasound echoes into electric signals. The receiving circuit 105 may receive the ultrasound echo signals converted into electric signals and send the ultrasound echo signals to the beam-forming unit 106. In the beam-forming unit 106, focus delay, weighting and channel summation may be performed on the ultrasound echo signals. Thereafter, signal processing may be performed on the ultrasound echo signals in the signal processing unit 107. The signals processed by the signal processing unit 107 may be sent to the three-dimensional imaging unit 108. By the processing in the three-dimensional processing unit 108, visual information such as three-dimensional images etc. may be obtained, which may be sent to the display 109.

After the probe 102 performs the scanning for one scan cycle, the signals processed by the signal processing unit 107 may form one volume of three-dimensional volume data in polar coordinate. The three-dimensional volume data in polar coordinate may be reconstructed to convert the polar coordinate volume data into Cartesian coordinate volume data, thereby obtaining a volume of three-dimensional volume data in Cartesian coordinate. Then, the three-dimensional unit 108 may process the three-dimensional volume data in Cartesian coordinate to obtain the visual information. The visual information may be displayed on the display 109.

The three-dimensional imaging unit 108 of the three-dimensional ultrasound imaging device in the present embodiment may further include a sub-unit which may be used to automatically extract the median sagittal section image of the fetus. This sub-unit may automatically extract the median sagittal section image from the obtained three-dimensional volume data of the head of the fetus, and process the median sagittal section image to detect the orientation of the fetal head in the median sagittal section image (for example, the fetal head and/or the fetal face is towards the top, towards the top left, towards the top right, towards the left, towards the right, towards the bottom, towards the bottom left, towards the bottom right or towards other direction, etc.). Thereafter, the sub-unit may rotate the median sagittal section image such that, in the rotated median sagittal section image, the fetal head is in a pre-set orientation (for example, the top of the fetal head is towards the top or the bottom or any other desired direction, or the fetal face is towards the top or the bottom or any other desired direction, etc., so as, for example, to facilitate the observation of the doctor or be suitable for the habits of the doctor, etc.), and/or mark the detected orientation of the fetal head in the median sagittal section image and display the processed median sagittal section image (described in detail below).

Figure 2:
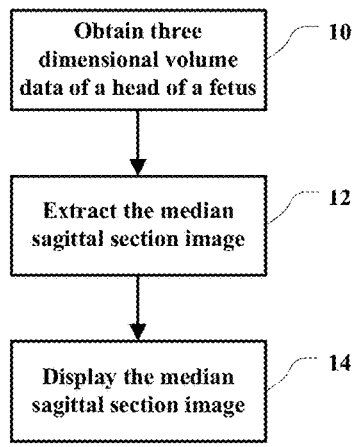
FIG. 2 is a flow chart of a three-dimensional ultrasound imaging method in one embodiment.
Figure 3:
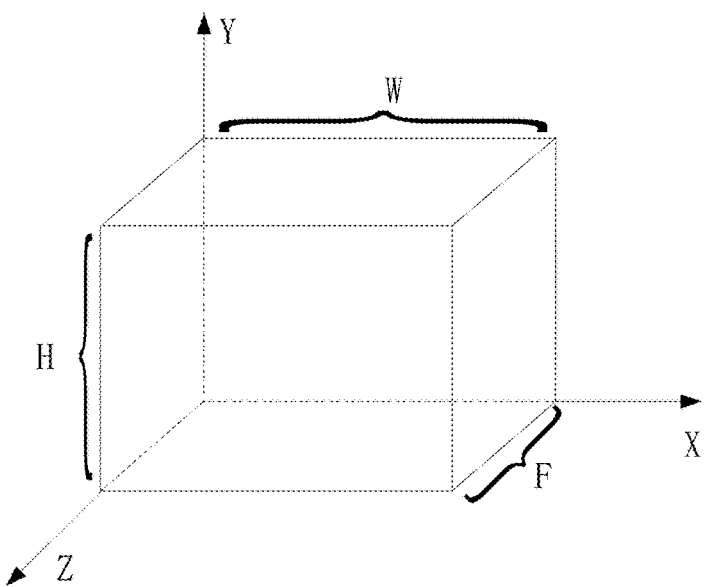
FIG. 3 schematically shows a three-dimensional volume data in one embodiment.

The flow chart of a three-dimensional ultrasound imaging method implemented by the three-dimensional ultrasound imaging device provided in the present embodiment is shown in FIG. 2. In step 21, the three-dimensional ultrasound imaging device may perform three-dimensional scanning on the fetal head. The three-dimensional ultrasound imaging device may transmit the ultrasound beams to the fetal head and receive the ultrasound echoes to obtain the ultrasound echo signals. The ultrasound echo signals may be processed as described above to obtain the three-dimensional volume data of the fetal head (referred to as "three-dimensional volume data" hereinafter). The specific steps for three-dimensionally scanning the scanning target and processing the ultrasound echo signals to obtain the three-dimensional volume data may be similar to the three-dimensional scanning and imaging methods and will not be described in detail here. By step 21, at least one volume of three-dimensional volume data of the fetal head may be obtained. For example, a volume of three-dimensional volume data may be shown in FIG. 3. The volume of three-dimensional volume data may include F frames of images, each of which may have a size of W×H, where W is the width of the image and H is the height of the image. In addition, in FIG. 3, the width direction of the image may be defined as the X direction, the height direction of the image may be defined as the Y direction, and the arrangement direction of the multiple frames of image may be defined as the Z direction. However, the X, Y, and Z directions may also be defined in other ways.

After the three-dimensional volume data is obtained in step 21, in one embodiment, it is desired to automatically extract the median sagittal section image of the fetal head from the three-dimensional volume data.

Figure 4:
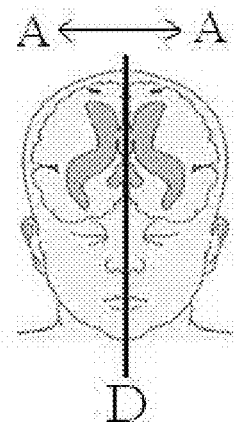
FIG. 4 schematically shows the position of the median sagittal section in a fetal head.
Figure 5:
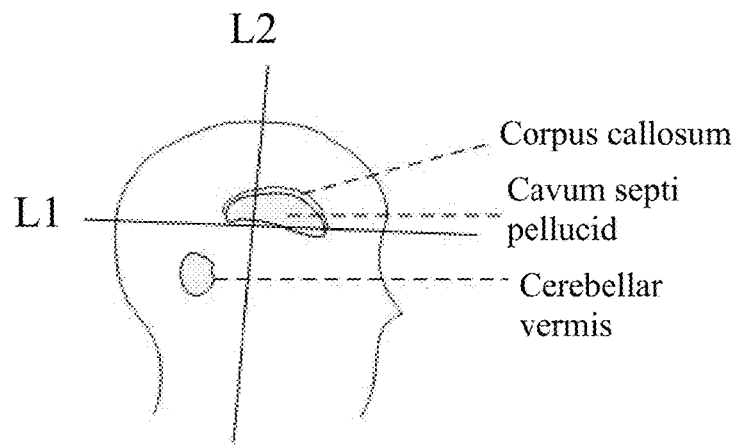
FIG. 5 schematically shows a median sagittal section image of a fetal head.
Figure 6:
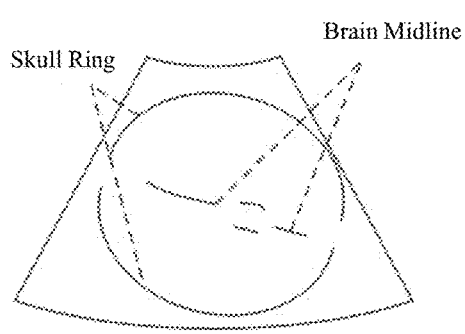
FIG. 6 schematically shows the image of the section L1 in FIG. 5.
Figure 7:
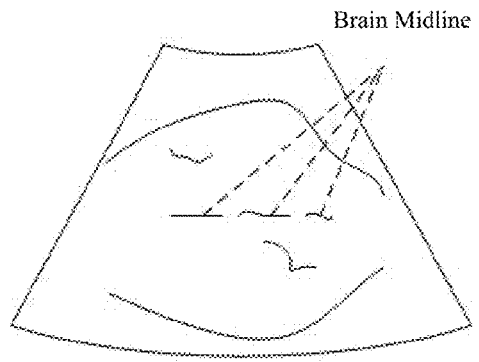
FIG. 7 schematically shows the image of the section L2 in FIG. 5.

FIG. 4 schematically shows the position of the median sagittal section in a fetal head, where the line D represents the median sagittal section of the fetal head. FIG. 5 shows a schematic view of a median sagittal section image of a fetal head, which shows that the image of the median sagittal section will include important information about the corpus callosum, the cerebellar vermis and the cavum septi pellucid (CSP) of the fetus. Furthermore, the cisterna cerebellomedullaris, the interthalamic adhesion, and the fourth ventricle, etc. of the fetus may also be observed in the median sagittal section image of a fetal head. Therefore, automatically extracting and displaying the median sagittal section image of a fetal head can provide important information to the doctors and thus greatly facilitate the observation of the doctors to the fetus. FIG. 6 and FIG. 7 schematically show the schematic views of the section images L1 and L2 which are perpendicular to the median sagittal section image of a fetal head, respectively.

The inventors have found that, among the images of a fetal head, the median sagittal section image has some special characteristics. For example, among all section images of the three-dimensional image of a fetal head, the median sagittal section image as a whole has larger gray value than surrounding areas. That is, in the three-dimensional image of a fetal head, the median sagittal section image appears as a section image which obviously has larger gray value than the surrounding areas, in other words, which has larger brightness than the surrounding areas. In addition, in a fetal head, the tissue structures outside both sides of the median sagittal section are approximately symmetrical with respect to the median sagittal section. Therefore, the image data of the three-dimensional image of a fetal head outside both sides of the median sagittal section image will have approximate symmetry with respect to the median sagittal section image. Furthermore, in a fetal head, the median sagittal section is located at the center position of the fetal head. Therefore, in the three-dimensional image of a fetal head, another section image which intersects with the median sagittal section image will contain information of the intersection line of said another section image with the median sagittal section image. In said another section image, the intersection line of said another section image with the median sagittal section image appears as a line with higher brightness, i.e. the brain midline. The collection of the brain midlines will form the median sagittal section image. In some embodiments of the present disclosure, these characteristics of the median sagittal section image of a fetal head may be used to detect or identify the median sagittal section image from the three-dimensional volume data of a fetal head.

Accordingly, in one embodiment, in step 23, a median sagittal section image may be extracted from the three-dimensional volume data obtained in step 21 using the characteristic(s) of the median sagittal section image of a fetal head (for example, the gray characteristic).

In the present embodiment, the entire or a part of the three-dimensional volume data of the fetal head of obtained in step 21 may be used to acquire the median sagittal section image. For example, the part of the three-dimensional volume data where the median sagittal section is most likely located may be used to extract the median sagittal section image, while the part where it is obviously impossible for the median sagittal section to be located may be excluded from the extraction process. For example, since the median sagittal section of a fetal head is a longitudinal section (i.e., a section in the direction from the top to the neck) located at the center position of a fetal head, it will be impossible for the median sagittal section image to be located in the regions at the edge of the fetal head. Such regions thus can be excluded from the extraction process.

In the embodiments, a variety of methods may be used to extract the median sagittal section image from the three-dimensional volume data. For example, as mentioned above, the median sagittal section image will have larger gray value than surrounding areas in the three-dimensional volume data. Therefore, in one embodiment, this characteristic may be used to extract the median sagittal section image from the three-dimensional volume data using digital image processing methods, such as image segmentation methods.

In one embodiment, the automatic extraction of the sagittal section image may essentially be indicating the location of the sagittal section image in the three-dimensional volume data. However, the expression of the result of the extraction may vary, such as the plane equation, the translation (in X, Y and Z directions) and rotation (about the X axis, Y axis and Z axis) of the sagittal section image with respect to the origin of the coordinate system, the transformation matrix of the sagittal section image with respect to the original coordinate system (in general one 4×4 matrix can represent the transformation relation between two coordinate systems), and even the spatial coordinates of three points (since three points can determine a plane), etc. These expressions may essentially be indication of the location of a plane in the coordinate system of a three-dimensional volume data, and may be converted to each other. In the embodiments, the expression of plane equation is used for the convenience of description. However, the present disclosure is not limited to the expression of the plane equation. Rather, other expressions described above or in the art may also be used. The expressions of the result of the extraction of the sagittal section image only differ in form, which does not affect the substance of the present disclosure, and therefore are all considered within the scope of the present disclosure.

Figure 8:
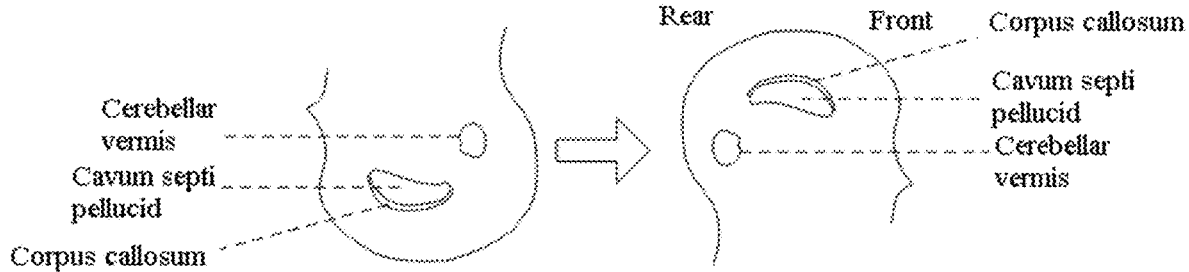
FIG. 8 schematically shows the median sagittal section images in which the fetal head is upside down and upright, respectively.

After the median sagittal section image of the fetal head is extracted, it may be displayed on the display so as to facilitate the observation of the doctor to the fetal head. However, due to the fetal position and the direction of the probe, the extracted median sagittal section image may be upside down (i.e. the fetal head is towards the bottom of the image, as shown in left view of FIG. 8) or in other orientation not suitable for the observation of the doctor. Since the median sagittal section image is very difficult to be obtained using conventional two-dimensional ultrasound imaging, most doctors are not familiar with the median sagittal section image. Furthermore, the resolution of the median sagittal section image is generally poor. Therefore, there are difficulties for the doctors to identify the median sagittal section image. If the extracted median sagittal section image is upside down or in other orientation not suitable for the observation by the doctor. Therefore, in the present embodiment, after the median sagittal section image of the fetal head is extracted, in step 25, the orientation of the fetal head in the median sagittal section image (for example, the fetal head and/or the fetal face is towards the top, towards the top left, towards the top right, towards the left, towards the right, towards the bottom, towards the bottom left, towards the bottom right or towards other direction, etc.) may further be detected. When it is detected that the orientation of the fetal head in the median sagittal section image is not convenient for the doctor to observe, the median sagittal section image may be rotated such that in the rotated median sagittal section image the fetal head is in a predetermined or desired orientation (for example, the top of the fetal head is towards the top or the bottom or any other desired direction, or the fetal face is towards the top or the bottom or any other desired direction, etc., so as to, for example, facilitate the observation of the doctor or be suitable for the habits of the doctor, etc.), and/or the detected orientation of the fetal head may be marked in the median sagittal section image. When displaying the median sagittal section image (i.e. step 29), the rotated or marked median sagittal section image may be displayed so as to facilitate the observation of the doctor, as shown in FIG. 8.

In one embodiment, the orientation of the fetal head in the median sagittal section image may be obtained by the image regions representing specific tissue areas of the fetal head in the median sagittal section image and/or in the section image in the three-dimensional volume data which is parallel to or intersects with the median sagittal section image.

In one embodiment, the specific tissue areas may be at least two specific tissue areas which have certain mutual positional relationship in the fetal head (such as eye and nose, eye and mouth, mouth and nose, eye, nose and/or mouth and cavum septi pellucid, or eye, nose and/or mouth and other tissue of the fetal head, etc.). In the present embodiment, at least two image regions representing at least two of these tissue areas may be extracted or detected from the median sagittal section image and/or from the section image which is parallel to or intersects with the median sagittal section image, and the orientation of the fetal head may be determined based on the mutual positional relationship of these image regions (for example, in the fetal head, the top of the head is always in the direction from mouth to eye, from mouth to nose or from nose to eye, etc.). When the mutual positional relationship of these image regions is determined, the orientation of the fetal head may be determined according to the mutual positional relationship.

In one embodiment, the specific tissue areas may be the tissue areas in the fetal head which have directional characteristics. In the present disclosure, the tissue area having directional characteristics may be the tissue area which itself or whose position contains the information being able to indicate the orientation of the fetal head, such as the skull or the skullcap (whose bending direction indicates the orientation of the fetal head), the cavum septi pellucid (whose orientation and position can indicate the orientation of the fetal head), or mouth, eye and nose (which are always located at the face side of the fetal head, thereby the orientation of the fetal head may be indicated by the position thereof), etc.

In these embodiments, one or more image regions representing the tissue areas may be extracted or detected from the median sagittal section image and/or from the section image which is parallel to or intersects with the median sagittal section image, and the orientation of the fetal head may be determined according to the positions and/or shapes of these image regions (for example, the positions or side at which the eye and the mouth are located are always the front portion or front side of the fetal head, and the orientation of the head may be determined according to the bending direction of the skull, etc.). Hereinafter, examples will be described in which the skull and the cavum septi pellucid serve as the specific tissue areas.

Figure 9:
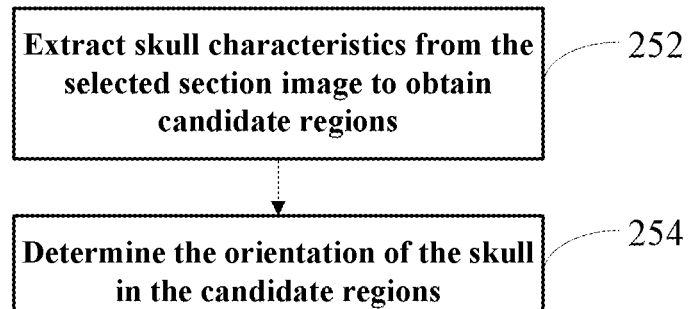
FIG. 9 is a flow chart for determining the orientation of the fetal head in the median sagittal section image in one embodiment.
Figure 10:
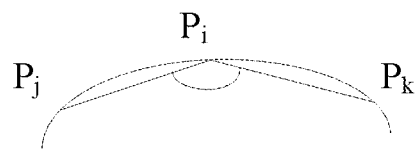
FIG. 10 schematically shows the determination of the orientation of the skull.

In one embodiment, the orientation of the fetal head in the median sagittal section image may be detected or identified utilizing the structures in the three-dimensional volume data which have directional characteristics. The applicant found that the skull is represented as high brightness in the three-dimensional image of the fetal head. Therefore, the orientation of the skull may be used to determine the orientation of the fetal head. In the present embodiment, the orientation of the skull in the median sagittal section image or in the image parallel to the median sagittal section image may be detected to determine the orientation of the fetal head. The process of the detection is shown in FIG. 9.

Step 252: extracting skull characteristics from selected section image to obtain candidate regions representing the skull. Since in the ultrasound image the skull is represented as high brightness while the brightness of the area at both sides of the skull reduced gradually, multiple methods for extracting the skull characteristics may be designed based on such feature. For example, in one embodiment, based on the high brightness of the skull area, the regions whose gray-scale values are greater than a pre-set threshold may be selected in the selected section images as the candidate regions of the skull. The selected section images may be the median sagittal section image and/or at least one section image which are parallel to the median sagittal section image. The threshold may be determined according to the actual needs. For example, the threshold may be an experience threshold, or may also be determined according to the statistical characteristics of the image. For example, the threshold may be set as equal to the mean of gray value multiplied by an experience coefficient. In another embodiment, based on the characteristics that the skull area is bright in middle and dark at both sides, operators may be designed based on differential. The convolution of the operators with the selected section image may be performed, and then the portion whose convolution values are greater than a pre-set threshold may be retained as the characteristics image. The operators designed based on differential may be one or more of the following operators:

$$\begin{bmatrix} -1 & -1 & -1 \\ 2 & 2 & 2 \\ -1 & -1 & -1 \end{bmatrix} \quad (1)$$

$$\begin{bmatrix} -1 & \ldots & -1 \\ & 0 & \\ 2 & \ldots & 2 \\ & 0 & \\ -1 & \ldots & -1 \end{bmatrix} \quad (2)$$

$$\begin{bmatrix} -1 \\ 0 \\ \ldots \\ 0 \\ 2 \\ 0 \\ \ldots \\ 0 \\ -1 \end{bmatrix} \quad (3)$$

$$\begin{bmatrix} 1 & 2 & 1 \\ 0 & 0 & 0 \\ -1 & -2 & -1 \end{bmatrix} \quad (4)$$

$$\begin{bmatrix} -1 & -2 & -1 \\ 0 & 0 & 0 \\ 1 & 2 & 1 \end{bmatrix} \quad (5)$$

After the characteristics extraction, generally multiple connected characteristics regions may be retained in the characteristics image. Therefore, one or more connected characteristics regions may be retained as the candidate regions based on certain rules. For example, the rules may be that the one or more characteristics regions of which the sum of the characteristics values are maximum are selected as the candidate regions. The characteristics values may be the characteristics used for extracting the skull characteristics above, such as the gray value characteristics. The characteristics values may also be the characteristics commonly used in characteristics extraction in digital image processing, such as the texture characteristics. In one embodiment, the rules may be that one or more characteristics regions of which the average characteristics values are maximal are selected as the candidate regions. In another embodiment, machine learning methods may be used, in which the characteristics may be extracted from the characteristics regions, the extracted characteristics may be inputted into a pre-trained classifier to be classified, and the candidate regions may be determined based on the classification results. The extracted characteristics herein may be the gray value averages of the characteristics regions, the characteristics value averages, the curvatures of the characteristics regions, entropy of the characteristics regions, the first moment or the second moment, etc. The pre-trained classifier may be obtained by extracting the characteristics mentioned above from a certain number of samples and performing the training using PCA (Principal Component Analysis), KPCA (Kernel Principal Component Analysis), ICA (Independent Component Analysis), LDA (Linear Discriminant Analysis), SVM (Support Vector Machine) or other classifier. The implementation of the classifier may be similar to those in image processing and pattern recognition techniques and will not be described in detail here. It shall be understood that, in the case that the number of the selected section images is greater than 1 (i.e. multiple section images are selected) the definition of the rules may be similar. For example, one or more characteristics regions whose sums of characteristics values or the characteristics value averages are maximum may be selected as the candidate regions of the skull, or the machine learning methods may be used to identify the candidate regions.

In step 254, in the candidate regions, the bending direction of the skull may be used to determine the orientation of the skull. Many methods may be used to determine the bending direction of the skull. For example, a quadratic curve may be used to fit the connected regions, and the orientation of the skull may be determined according to the coefficient of the quadratic term of the quadratic curve. For example, in the case that the coefficient of the quadratic term is greater than 0, the skull is towards the bottom, on the contrary, the skull is towards the top. In another embodiment, machine learning methods may be used, which may be obtained by training using PCA, KPCA, LDA, SVM or other methods. In the case of multiple candidate connected regions, the orientation of each connected region may be respectively determined and the final orientation of the skull may be determined by vote.

After the orientation of the fetal head is determined, in the case that the fetal head is towards the bottom, the median sagittal section image may be rotated by 180 degree or be upside down and then be displayed, such that the displayed image is more suitable for observation, thereby facilitating the observation of the doctor to the fetus.

In the embodiments above, the plane equation is used to express the results of the extraction for the convenience of description. However, the present disclosure is not limited to the plane equation. Other methods mentioned above or in the art may also be used. The expression of the results of the sagittal section image only differ in form, but will not affect the essence of the present disclosure.

In some embodiments, the three-dimensional ultrasound imaging system implementing the methods above will not be limited to the ultrasound imaging system integrated as a single device (for example the cart ultrasound imaging system or portable ultrasound imaging system), but may also be a distributed system. For example, at least a portion of the steps or functions of the methods above may be implemented in other device which is connected (wired or wirelessly) to the cart ultrasound imaging system or portable ultrasound imaging system through data communication device. Said other device may be, for example, data processing workstation, personal computer, various smart portable devices, other ultrasound imaging device or various network server, etc. Therefore, the three-dimensional ultrasound imaging system in the present disclosure may be formed by the device implementing the at least a portion of the steps or functions and the cart ultrasound imaging system or the portable ultrasound imaging system.

With the ultrasound imaging methods of the embodiments above, ultrasound scanning may be performed on the fetus to obtain the three-dimensional volume data of the fetal head, and the median sagittal section image of the fetal head may be automatically extracted according to the obtained three-dimensional volume data and the orientation of the fetal head may be automatically determined (for example, determining whether the fetus is upside down). In the case that the fetus is upside down, the median sagittal section image may be rotated such that it is upright. Therefore, the displayed median sagittal section image will be suitable for observation of human, and the issue that it is difficult for the doctor to accurately find out the median sagittal section image manually may be solved. Accordingly, the doctor can conveniently observe the median sagittal section image of the fetal head.

The three-dimensional ultrasound imaging methods or systems provided by the present embodiment may be similar to those in the embodiments above. The difference is that, in step 25 of the embodiments above, the orientation of the fetal head in the median sagittal section image may be determined according to the orientation of the skull, while in step 25 of the present embodiment, the orientation of the fetal head in the median sagittal section image may be determined according to the orientation of the cavum septi pellucid.

As shown in FIG. 5 and FIG. 8, in the ultrasound image, the shape of the cavum septi pellucid is crescent. When the fetus in the ultrasound image is upright, the cavum septi pellucid is represented as an upwardly convex crescent. On the contrary, when the fetus in the ultrasound image is upside down, the cavum septi pellucid is represented as a downwardly convex crescent. Therefore, the orientation of the cavum septi pellucid may be used to determine the orientation of the fetal head in the median sagittal section image.

Figure 11:
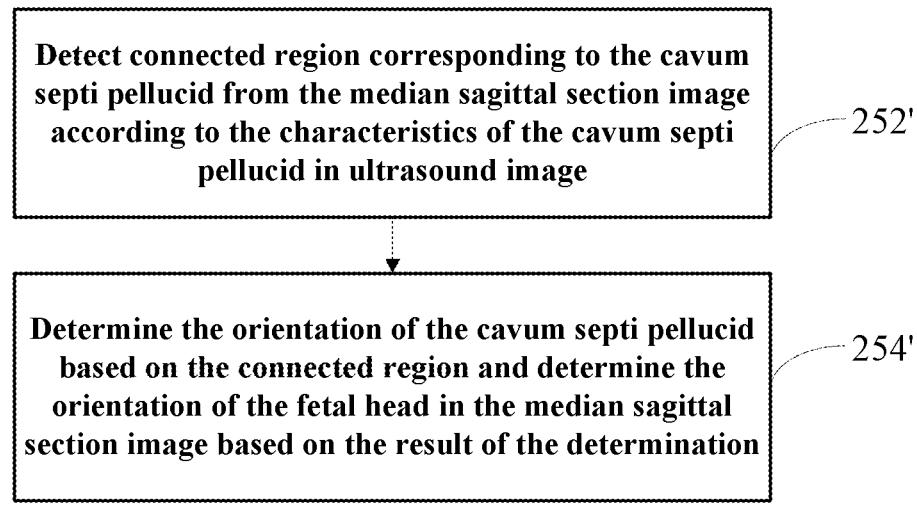
FIG. 11 is a flow chart for determining the orientation of the fetal head in the median sagittal section image in one embodiment.

In the present embodiment, the process of determining the orientation of the fetal head in the median sagittal section image according to the orientation of the cavum septi pellucid may include step 252' and step 254', as shown in FIG. 11.

In step 252', the connected region corresponding to the cavum septi pellucid may be detected from the median sagittal section image according to the characteristics of the cavum septi pellucid in ultrasound image.

In step 252', since the cavum septi pellucid is represented as dark area while its surrounding areas generally have higher brightness in the ultrasound image, multiple methods may be designed based on such characteristics to segment the dark area, thereby detecting the cavum septi pellucid. For example, image segmentation algorithms may be used to segment the region which may be considered as the cavum septi pellucid, such as threshold segmentation, Snake algorithm, level-set algorithm or graph-cut segmentation, etc. Generally, multiple regions may be obtained by the segmentation. Therefore, certain rules may be set to select the region which is most similar to the cavum septi pellucid. For example, it may be determined according to the shape, grayscale value, variance or other characteristics, or the combination thereof, thereby obtaining the connected region corresponding to the cavum septi pellucid.

In step 254', the orientation of the cavum septi pellucid may be determined based on the connected region and the orientation of the head of the fetus in the median sagittal section image may be determined based on the result of the determination.

In step 254', the methods similar to them methods for determining the orientation of the skull in the embodiments above may be used to determine the orientation of the cavum septi pellucid based on the connected region corresponding to the cavum septi pellucid.

For example, methods similar to steps 254a1 to 254a3 may be used to determine the orientation of the cavum septi pellucid. First, mathematical morphology processing may be performed on the connected region corresponding to the cavum septi pellucid to extract the skeleton of the connected region to obtain a skeleton image. Thereafter, a longest, continuous curve may be searched in the skeleton image, which may be a representative curve. The orientation of the cavum septi pellucid may be determined based on the coordinates of at least one point in the middle and at least one point at the end of the searched curve.

In one embodiment, methods similar to steps 254b1 to 254b2 may be used to determine the orientation of the cavum septi pellucid. First, a middle line in vertical direction of the connected region corresponding to the cavum septi pellucid may be obtained. Thereafter, the orientation of the cavum septi pellucid may be determined using methods similar to step 254a3.

Based on the determined orientation of the cavum septi pellucid, in the case that the cavum septi pellucid is upwardly convex, the head of the fetus in the median sagittal section image is towards the top, while in the case that the cavum septi pellucid is downwardly convex, the head of the fetus in the median sagittal section image is towards the bottom. In the case that the head is towards the bottom, the median sagittal section image may be rotated by 180 degree or be upside down, such that the displayed image may be more suitable for observation, thereby facilitating the observation of the doctor to the fetus.

Figure 12:
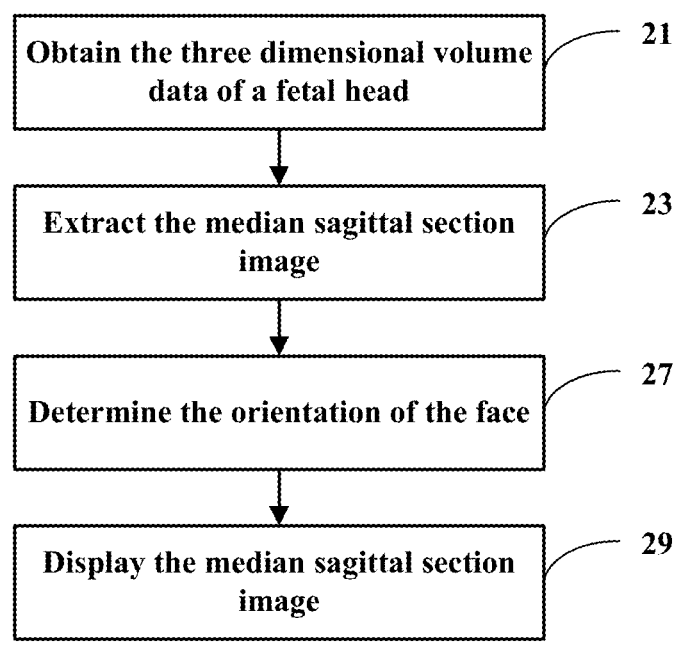
FIG. 12 is a flow chart of a three-dimensional ultrasound imaging method in one embodiment.

A three-dimensional ultrasound imaging method in one embodiment is shown in FIG. 12. The method may include obtaining the three-dimensional volume data of the fetal head (step 21), extracting the median sagittal section image (step 23), determining the orientation of the fetal face (step 27) and displaying the median sagittal section image (step 29). The steps 21, 23 and 29 may be similar to those in the embodiments above and will not be described herein. In the present embodiment, a three-dimensional ultrasound imaging device which implements the method of the present embodiment may also be provided. Except the three-dimensional imaging unit, this three-dimensional ultrasound imaging device may be similar to that in the embodiments above and will not be described in detail again herein.

Since the cavum septi pellucid is located in the front of the brain, the face and back of the fetus (i.e., the orientation of the fetal face) may be determined according to the location of the cavum septi pellucid.

Figure 13:
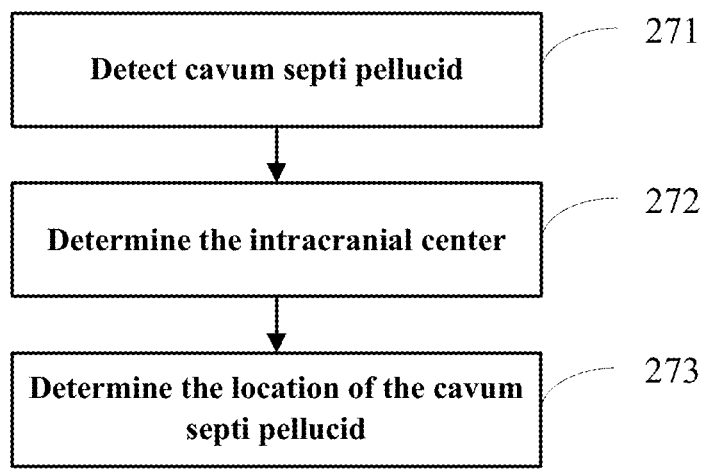
FIG. 13 is a flow chart for determining the orientation of the face in one embodiment.

In the present embodiment, the flow chart of step 27 may be as shown in FIG. 13, which may include detecting the cavum septi pellucid (step 271), determining the intracranial center (step 272) and determining the location of the cavum septi pellucid (step 273).

In step 271, the cavum septi pellucid may be detected using a method similar to those for detecting the cavum septi pellucid in the embodiments above. For example, an image segmentation algorithm may be performed on the median sagittal section image to obtain at least one region, and the region which is most similar to the cavum septi pellucid in region characteristics may be selected as the cavum septi pellucid region. The specific processes may be similar to step 252' above and will not be described in details again.

In step 272, the intracranial center may be determined according to the fetal skull in the volume data. In the volume data, the fetal skull may be represented as an approximate ellipsoid or ellipse, and be represented as high brightness region in ultrasound image. Therefore, in one embodiment, the determination of the intracranial center may include steps 272a1 to 272a3.

In step 272a1, at least one frame of A section image (i.e., horizontal section image obtained along A-A in FIG. 4) may be selected from the volume data.

In step 272a2, operators may be designed based on differential, such as one or more of the operators (1) to (5) above, and characteristics extraction may be performed on the A section image using the designed operator.

In step 272a3, ellipsoid or ellipse detection may be performed on the extracted characteristics. Any ellipse detection method may be used, such as least squares estimation method, Hough transform method or random Hough transform method, etc. For example, The Hough transform method described below may be used to detect the ellipsoid or ellipse.

After the ellipse or the ellipsoid id detected, the center of the ellipse or the ellipsoid may be determined according to related geometric knowledge.

In step 273, the coordinate of the region of the cavum septi pellucid may be compared with the coordinate of the center, and the orientation of the fetal face in the median sagittal section image may be determined based on the result of the comparison. Specifically, the location of a certain point (whose coordinate on the X axis may be x) in the region of the the cavum septi pellucid may be selected as the location of the cavum septi pellucid, such as the central location of the cavum septi pellucid region detected in step 271 or other location. Assuming that the coordinate of the center of the ellipse or ellipsoid obtained in step 272 in X axis is xcenter, x may be compared with xcenter. In the case of x<xcenter, it is indicated that the cavum septi pellucid is located on the left of the intracranial center in the median sagittal section image, i.e., the front portion (face) of the fetus is located at the left portion of the median sagittal section image while the rear portion (back) of the fetus is locate at the right portion. In the opposite case, the rear portion (back) of the fetus is located at the left portion of the median sagittal section image while the front portion (face) of the fetus is locate at the right portion.

Figure 25:
FIGS. 25 and 26 schematically show the icons used for marking the orientation of the fetal head in one embodiment.
Figure 26:
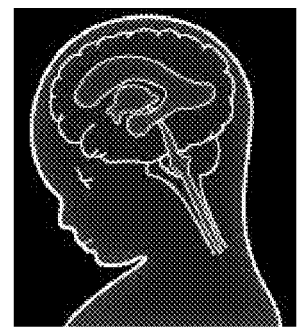

Based on the determined orientation of the fetal head (e.g., the orientation of the face or the top of the head, etc.) in the median sagittal section image, the front portion and/or the rear portion of the fetus may be marked on the median sagittal section image, as shown in the view on the right of FIG. 8. Alternatively, in one embodiment, a fetal head icon may be used to indicate the orientation of the front portion/real portion or the top of the head or the face of the fetus, as shown in FIGS. 25 and 26, where the orientation of the face of the icon may represent the orientation of the face in current image. The median sagittal section image in which the orientation of the fetal head (e.g., the front portion and/or real portion of the fetus, etc.) is marked may be display on the display, thereby facilitating the observation of the doctor to the fetus.

Figure 14:
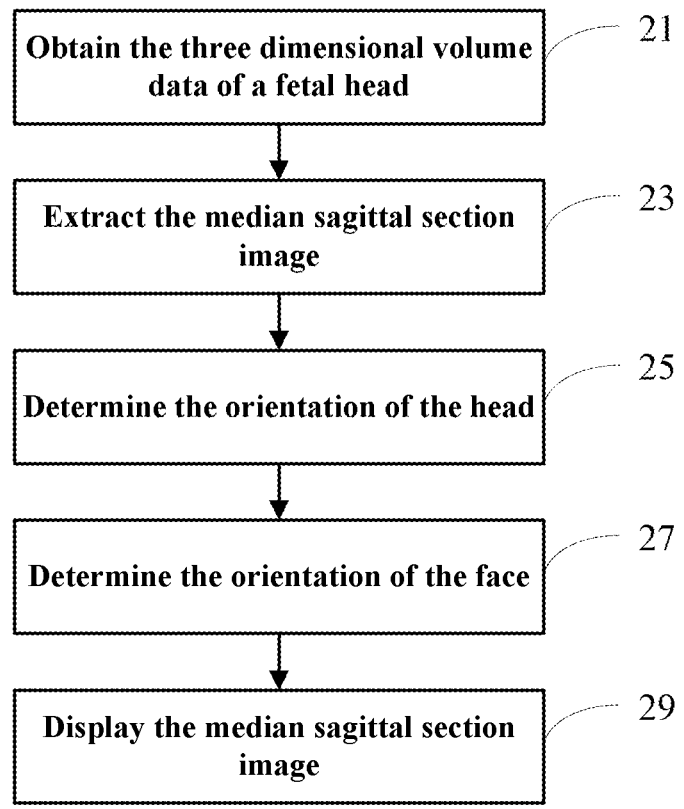
FIG. 14 is a flow chart of a three-dimensional ultrasound imaging method in one embodiment.

FIG. 14 schematically shows a flow chart of a three-dimensional ultrasound imaging method in one embodiment. The steps of this method may be similar to those in the embodiments above and will not be described in detail again. It should be understood that the order of step 25 and step 27 can be reversed, i.e., the orientation of the face may be determined first, and then the orientation of the head may be determined. In the present embodiment, the orientation of the fetal head and the fetal face may be determined, such that the doctor can more easily identify the tissues in the sagittal section image.

The processes for extracting the median sagittal section image in step 23 in some embodiments will be described below.

Figure 15:
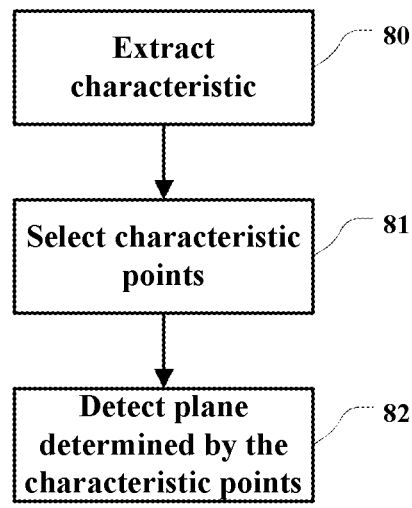
FIG. 15 is a flow chart for extracting the median sagittal section image in one embodiment.

In one embodiment, the flow chart of extracting the median sagittal section image from the three-dimensional volume data may be as shown in FIG. 15, which may include extracting characteristics (step 80), selecting characteristic points (step 81) and detecting a plane determined by the selected characteristic points (step 82).

As mentioned above, the median sagittal section image will have larger gray value than surrounding areas in the three-dimensional volume data. In one embodiment, this characteristic may be used to extract the median sagittal section image from the three-dimensional volume data. Therefore, in step 80, sagittal section characteristic regions which represent plane regions having larger gray values than the areas located outside both sides thereof may be extracted from the three-dimensional volume data. In other words, some characteristic regions may be extracted from the three-dimensional volume data. The characteristic regions may represent plane regions which have larger gray value than the areas located outside both sides of these plane regions. These extracted characteristic regions may be the sagittal section characteristic regions mentioned above. This way, the characteristic of "the median sagittal section image having larger gray value than surrounding areas" may be fully utilized to facilitate the extraction of the median sagittal section image.

A variety of suitable ways may be used to extract the sagittal section characteristic regions from the three-dimensional volume data. For example, in one embodiment, convolution may be performed on the three-dimensional volume data using a characteristic extraction operator to obtain a convolution image, which will contain the sagittal section characteristic regions extracted.

In one embodiment, the convolution may be performed on each frame image of the three-dimensional volume data using two-dimensional characteristic extraction operator, respectively, and then the obtained convolution images may be combined to form a three-dimensional convolution volume data. Alternatively, the convolution may also be performed directly on the three-dimensional volume data using a three-dimensional characteristic extraction operator designed therefor. The specific steps of the convolution may be well known in the art and thus will not be described in detail herein.

In the embodiments, the characteristic extraction operators may be designed according to the image characteristics to be extracted. For example, in the embodiments mentioned above, the sagittal section characteristic regions having larger gray value than the area outside both sides thereof need to be extracted. In this case, one or more of the characteristic extraction operators (1) to (5) in the embodiment above may be used.

In one embodiment, a characteristic extraction operator obtained by transposition (matrix transposition), rotation or combination of the characteristic extraction operators mentioned above may also be used. Alternatively, other suitable characteristic extraction operators, such as the Roberts operator, the Laplace Gauss operator or the modification thereof or the like, may also be used.

In one embodiment, a three-dimensional characteristic extraction operator may also be used.

In one embodiment, the size of the characteristic extraction operator (two-dimensional or three-dimensional) may be set as required.

After the sagittal section characteristic regions are extracted in the step 80, characteristic points which satisfy certain conditions may be selected from the extracted sagittal section characteristic regions in step 81. In general, at least three characteristic points may be selected. The characteristic point parameters of the selected characteristic points may be recorded, which will be used in following steps.

In one embodiment, the "characteristic point parameters" may include the coordinates and/or the value (for example, the gray value or the result value of convolution, etc.) of the characteristic points.

In one embodiment, the "certain conditions" mentioned above may be determined according to the properties of the characteristic extraction operator used. For example, when the characteristic extraction operators (1)-(5) mentioned above are used, the certain conditions may be that the result value of convolution of the point is larger than a certain threshold value. The threshold value may be an empirical parameter and may be determined as required.

In one embodiment, in order to facilitate the following plane detection step (described in details below) and reduce the impact of noise, the points which are obviously not within the head may be excluded according to certain prior knowledge. For example, the head usually is located at the center of the three-dimensional volume data. Therefore, the characteristic points may be selected from points which are located within a sphere or ellipsoid centered at the center of the three-dimensional volume data and having a radius of a threshold value. This threshold value may also be an empirical parameter or determined as required.

The characteristic points selected in the step 81 generally can determine a plane. In one embodiment, this plane may be the plane of the median sagittal section and the section image in the three-dimensional volume data which is coincide with this plane may be the median sagittal section image of the head of the fetus. Therefore, in one embodiment, the plane of the median sagittal section of the head of the fetus may be determined by acquiring the plane determined by the selected characteristic points.

The plane determined by a plurality of characteristic points may be acquired by various methods, such as weighted Hough transformation, random Hough transformation, least squares estimation, or Radon transformation, etc.

For example, in one embodiment, the weighted Hough transformation may be used to acquire the plane determined by the selected characteristic points, which will be described in details below.

In a three-dimensional space, a plane generally can be expressed as $aX+bY+cZ+d=0$ or $Z=aX+bY+C$ or $Y=aX+bZ+c$, where a, b, c and d are the plane parameters which determine the plane.

Figure 16:
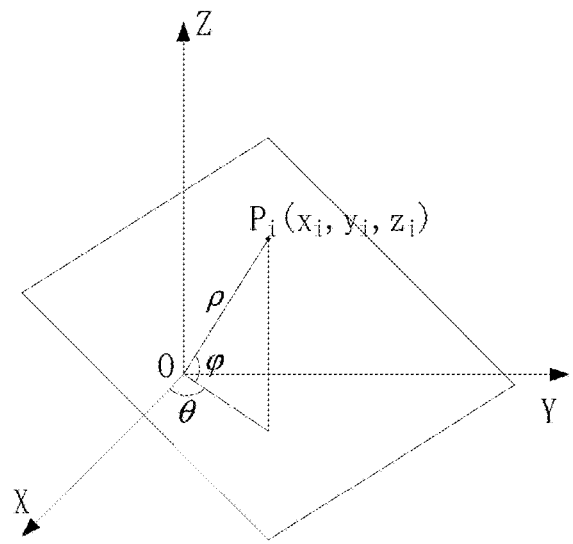
FIG. 16 schematically shows the plane and the plane parameters thereof in a three-dimensional space.

In a three-dimensional space, the plane may also be expressed as following formula:

$$\rho = \cos\theta \cos\varphi X + \sin\theta \cos\varphi Y + \sin\varphi Z \quad (6),$$

where $\theta$, $\varphi$ and $\rho$ are the plane parameters and their meaning may be those as shown in FIG. 16. One set of $\theta$, $\varphi$ and $\rho$ may determine one plane.

The plane parameters $\theta$, $\varphi$ and $\rho$ in the formula (6) have respective ranges which are related to the way for defining the three-dimensional Cartesian coordinate system. For example, in a three-dimensional volume data, when the position of the origin of the three-dimensional Cartesian coordinate system vary, the ranges of the plane parameters will vary correspondingly.

For example, in the embodiment shown in FIG. 16, the range of the parameter $\rho$ may be as following:

$$0 \leq \rho \leq \sqrt{(W-1)^2 + (H-1)^2 + (F-1)^2} \quad (7).$$

where W, H and F are the sizes of the three-dimensional volume data, F is the number of the frame images in the three-dimensional volume data, W is the width of the frame image, and H is the height of the frame image.

It will be understood that when the three-dimensional Cartesian coordinate system is defined in other ways, the ranges of the plane parameters $\theta$, $\varphi$ and $\rho$ will be different.

In the three-dimensional space corresponding to the three-dimensional volume data, there are infinite number of planes which pass through one certain point, i.e., there are infinite number of sets of $\theta$, $\varphi$ and $\rho$, which will form a parameter space (which may be referred to as $\theta$-$\varphi$-$\rho$ space), i.e., a Hough space. The concept of the Hough transformation is projecting the points in the three-dimensional space corresponding to the three-dimensional volume data into the Hough space and detecting the peak value of the Hough space. The peak value corresponds to the plane in the three-dimensional space corresponding to the three-dimensional volume data.

Figure 17:
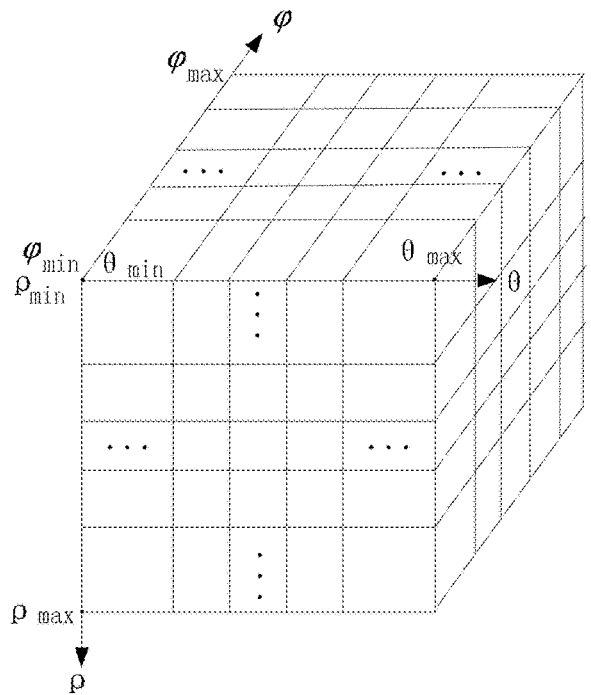
FIG. 17 schematically shows a three-dimensional Hough matrix in one embodiment.
Figure 18:
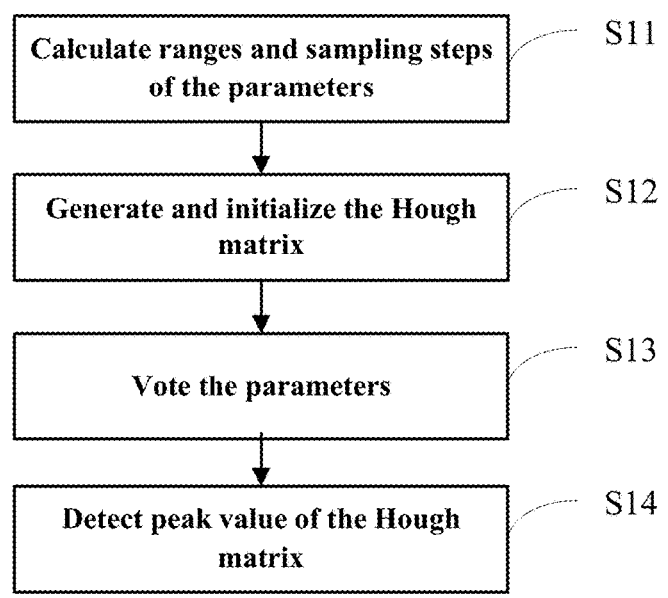
FIG. 18 schematically shows a process of a weighted Hough transform in one embodiment.

In one embodiment, $\theta$, $\varphi$ and $\rho$ are continuous. Therefore, $\theta$, $\varphi$ and $\rho$ may be sampled to be divided into a plurality of units (as shown in FIG. 17). Accordingly, the weighted Hough transformation may include steps S11 to S14 as shown in FIG. 18.

S11: calculating ranges and sampling steps of the plane parameters. The range of the parameter $\rho$ may be as shown in formula (7). The largest ranges of the parameter $\theta$ and $\varphi$ may be determined with reference to FIG. 16, such as, $0° \leq \theta < 360°$ and $-90° \leq \varphi \leq 90°$.

In one embodiment, the ranges may also be narrowed according to certain prior knowledge.

The ranges calculated may be expressed as $\theta_{min} \leq \theta \leq \theta_{max}$, $\varphi_{min} \leq \varphi \leq \varphi_{max}$ and $\rho_{min} \leq \rho \leq \rho_{max}$. The sampling steps $\theta$step, $\varphi$step and $\rho$step may be determined according to the extraction accuracy required. For example, in one embodiment, $\theta_{step}=1$, $\varphi_{step}=1$, $\rho_{step}=2$. In other embodiments, other suitable values may also be used.

S12: generating and initializing the Hough matrix. The Hough matrix may be generated and be initialized to zero. The size of a three-dimensional Hough matrix may be:

$$\frac{(\theta_{max} - \theta_{min})}{\theta_{step}} \times \frac{(\varphi_{max} - \varphi_{min})}{\varphi_{step}} \times \frac{(\rho_{max} - \rho_{min})}{\rho_{step}}. \quad (8)$$

In one embodiment, three one-dimensional Hough matrixes may also be used, the sizes of which may be $$\frac{(\theta_{max} - \theta_{min})}{\theta_{step}}, \frac{(\varphi_{max} - \varphi_{min})}{\varphi_{step}} \text{ and } \frac{(\rho_{max} - \rho_{min})}{\rho_{step}},$$

respectively.

S13: Voting the parameters. For example, a voting value $\rho l$ may be calculated as following for each of the selected characteristic points and each $\theta_j$ and $\varphi_k$ in the range aforementioned:

$$\rho_l = \cos\theta_j \cos\varphi_k X_i + \sin\theta_j \cos\varphi_k Y_i + \sin\varphi_k Z_i \quad (9).$$

where $(X_i, Y_i, Z_i)$ are the coordinates of the $i^{th}$ characteristic point Pi.

Then the Hough matrix may be updated as:

$$H(\theta_j, \varphi_k, \rho_l) = H(\theta_j, \varphi_k, \rho_l) + Vi \quad (10).$$

where Vi is the value of the $i^{th}$ characteristic point Pi (for example, the gray value or the result value of convolution, etc.).

S14: detecting peak value of the Hough matrix. The $\theta$, $\varphi$ and $\rho$ corresponding to the peak value of the Hough matrix H may be calculated. Provided that the location of the peak value of the Hough matrix H is $(\theta_j, \varphi_k, \rho_l)$, the plane acquired may be:

$$\theta=\theta_j\theta_{step}+\theta_{min}$$

$$\varphi=\varphi_k\varphi_{step}+\varphi_{min}$$

$$\rho=\rho_l\rho_{step}+\rho_{min} \quad (11).$$

In the embodiments aforementioned which use three one-dimensional Hough matrixes, the $\theta$, $\varphi$ and $\rho$ corresponding to the peak values of the Hough matrixes may be calculated respectively.

In these embodiments, the weighted Hough transformation takes into account the difference between the contributions of respective characteristic points Pi to the plane acquisition. The larger its value Vi, the more it contribute to the Hough matrix.

In one embodiment, the difference between the contributions of respective characteristic points may also not be taken into account. That is, the value Vi of every characteristic point may be set as 1. In this case, the plane determined by these characteristic points may also be acquired. In fact, in this case, the weighted Hough transformation aforementioned is degenerated into a traditional Hough transformation.

Figure 19:
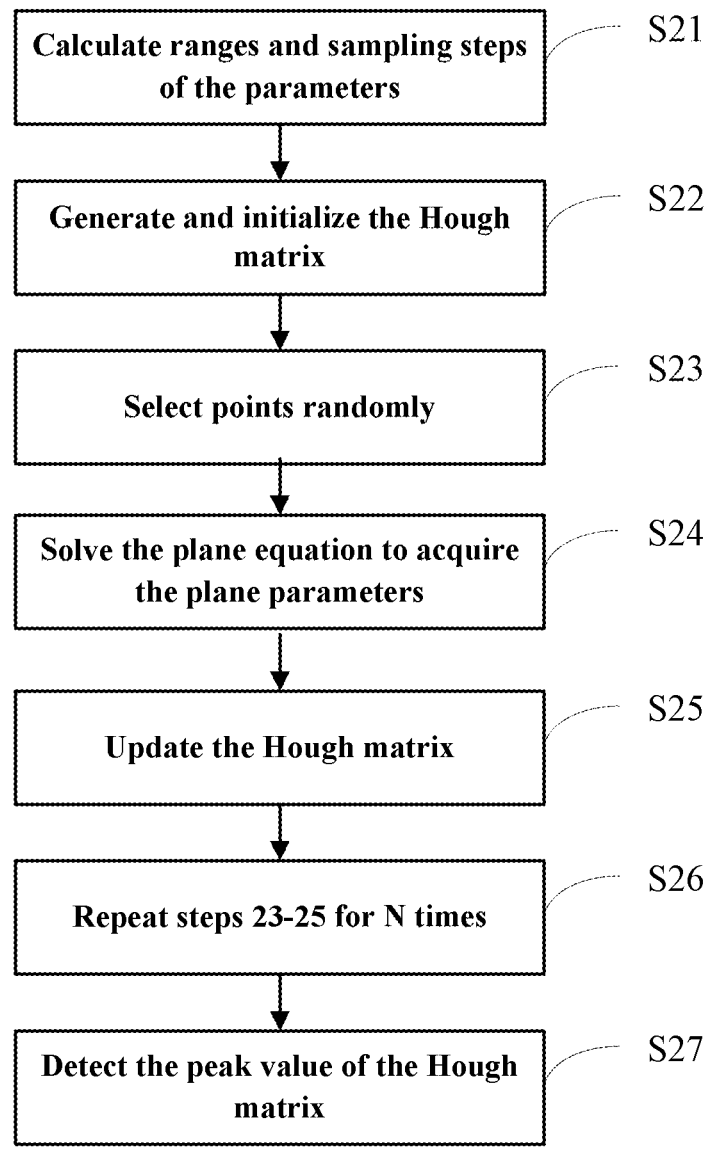
FIG. 19 schematically shows a process of a random Hough transform in one embodiment.

In one embodiment, other methods for plane acquisition may also be used. For example, in one embodiment, the plane determined by the selected characteristic points may be acquired by random Hough transformation, which may include steps S21 to S27, as shown in FIG. 19.

S21: calculating ranges and sampling steps of the plane parameters. In this step, the ranges and the sampling steps of the plane parameters $\theta$, $\varphi$ and $\rho$ may be calculated. This step may be the same as or similar to the step S11 aforementioned.

S22: generating a Hough matrix and initializing it to zero. In this step, a three-dimensional Hough matrix may be generated and be initialized to 0. This step may be the same as or similar to the step S12 aforementioned.

S23: selecting points randomly. In this step, three points may be selected randomly from the selected characteristic points.

S24: solving the plane equation to acquire the plane parameters. In this step, the coordinates of the three points may be substituted into the plane equation to solve for the plane parameters $\theta$, $\varphi$ and $\rho$. The specific methods for solving for plane parameters are well known in the art and will not described in details herein.

S25: updating the Hough matrix. In this step, the values at the locations corresponding to the $\theta$, $\varphi$ and $\rho$ in the Hough matrix may be increased by 1.

S26: repeating the steps S23 to S25 for N times. N herein may be a predefined parameter, and may be set as required. For example, in one embodiment, N may be 50000. In other embodiments, N may be other value.

S27: detecting the peak value of the Hough matrix. In this step, the location in the Hough matrix which has maximum value may be acquired and the $\theta$, $\varphi$ and $\rho$ corresponding to the location represent the plane acquired.

Figure 20:
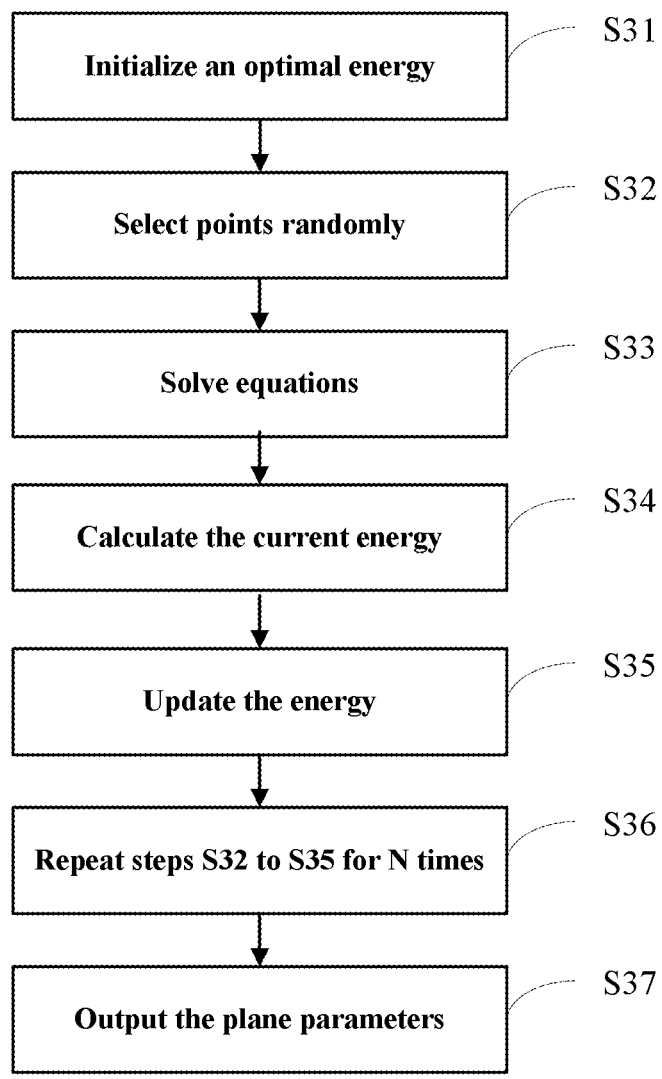
FIG. 20 schematically shows a process for detecting the plane determined by the selected characteristic points in one embodiment.

In one embodiment, another method (which is referred to as stochastic optimal energy method herein) for acquiring the plane determined by the selected characteristic points may include steps S31 to S37 as shown in FIG. 20.

S31: initializing an optimal energy E_best=0.

S32: selecting points randomly. In this step, three points may be selected randomly from the selected characteristic points.

S33: solving equations. In this step, the coordinates of the three points may be substituted into plane equations to solve for the plane parameters $\theta$, $\varphi$ and $\rho$.

S34: calculating current energy E. In this step, an "energy" E of the selected characteristic points from which the distances to the plane acquired in step S33 are less than $\varepsilon$ may be calculated.

In this step, the distance from each characteristic point Pi of the selected characteristic points to the plane $(\theta, \varphi, \rho)$ acquired in step S33 may be calculated. When the distance is less than $\varepsilon$, the value Vi of the current characteristic point may be accumulated to the energy E, i.e., E=E+Vi. $\varepsilon$ is a parameter which may be set as required. For example, in one embodiment, $\varepsilon$ may be set as 5. $\varepsilon$ may also be set as other value.

S35: updating the energy. If the current energy E>E_best, E_best may be set as E and the current plane parameters may be updated as the optimal plane parameters. Otherwise, it turns to step S36.

S36: repeating steps S32 to S35 for N times. N is iteration time and may be set as required.

S37: outputting the plane parameters. After the step S36 is completed, the plane parameters corresponding to the iteration with maximum energy may be outputted as acquired plane parameters.

In this way, one plane determined by the select characteristic points may be acquired.

In one embodiment, in the step S34, the value Vi of the current characteristic point may also not be accumulated. Rather, when the distance from point Pi to the plane is less than $\varepsilon$, E=E+1. That is, the contributions of the selected characteristic points to the plane acquisition are considered as to be the same.

In the embodiments above, the plane expression in formula (6) is used. The plane is acquired by calculating the coefficients 6, cps and p of the formula. However, the form of the plane expression does not affect the methods of the embodiments. The methods described above are also suitable for other plane expression such as aX+bY+cZ+d=0, Z=aX+bY+c or Y=aX+bZ+c after simple modification.

After the median sagittal section image of the fetal head is extracted using the methods of the embodiments above, the orientation of the fetal head and/or the fetal face may be determined with reference to the embodiments above. In the case that the head is upside down, the median sagittal section image may be adjusted such that the head is upright and/or the orientation of the face may be marked in the median sagittal section image. Thereafter the adjusted and/or marked median sagittal section image may be displayed in order to facilitate the observation of the doctor to the fetal head.

As described above and with further reference to FIG. 4 to FIG. 7, in the three-dimensional image of the head of the fetus, the median sagittal section is the longitudinal section located at the middle of the head of the fetus, and other section images which intersect with the median sagittal section image will contain information at the intersection position of said other section images with the median sagittal section image, in other words, will contain information at the intersection line. In said other section image, the intersection line of said other section image with the median sagittal section image appear as a line with higher brightness (because, as described above, in the three-dimensional image or the three-dimensional volume data of a fetal head, the median sagittal section image has larger brightness than surrounding areas), i.e., the brain midline. The collection of the brain midlines forms the median sagittal section image. Therefore, in some embodiments of the present disclosure, these characteristics may be used to acquire the median sagittal section image from the three-dimensional volume data.

Figure 21:
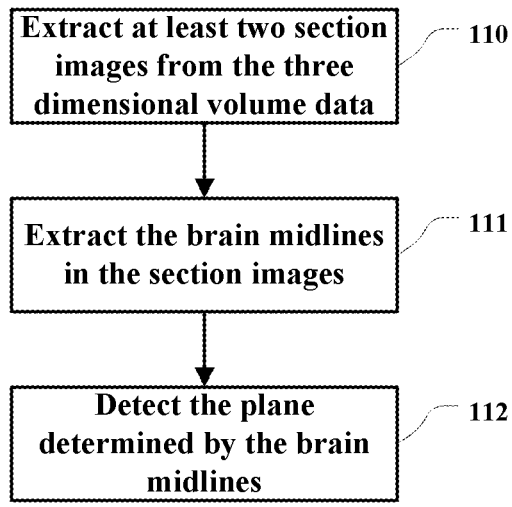
FIG. 21 schematically shows the flow chart for extracting the median sagittal section image in one embodiment.

For example, in one embodiment, a schematic flow chart of extracting the median sagittal section image from the three-dimensional volume data may be as shown in FIG. 21, which may include extracting at least two section images from the three-dimensional volume data (step 110), extracting brain midlines from the section images (step 111) and detecting the plane determined by the brain midlines (step 112).

In one embodiment, in step 110, at least two section images may be extracted from the three-dimensional volume data. The section images may be extracted in different ways. For example, the section images which are parallel to the section L2 in FIG. 5 and/or parallel to the section L1 in FIG. 5 may be extracted. Alternatively, any other suitable section images may be extracted, such as the section images which are at certain angles with respect to the section L2 and/or the section L1. The number of the extracted section images may also not be limited.

After the section images are extracted, in step 111, the brain midline may be extracted from each of the section images, thereby obtaining multiple straight lines representing the brain midline.

A brain midline appears as a straight line in a section image which has larger gray value than the areas outside both sides thereof. Therefore, the extraction of the brain midline may be achieved based on this characteristic.

Figure 22:
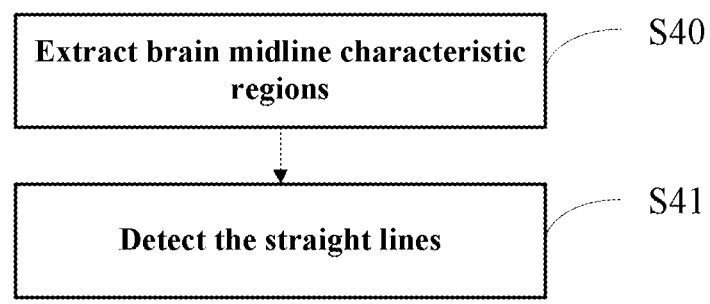
FIG. 22 is a flow chart for extracting the brain midline in one embodiment.

In one embodiment, extracting the brain midline from each of the extracted section image may include steps S40 to S41 as shown in FIG. 22.

S40: extracting brain midline characteristic regions.

In one embodiment, the brain midline characteristic regions which match the characteristics of the brain midline aforementioned, i.e., the brain midline characteristic regions which represent lines having larger gray value than areas outside both sides thereof, may be extracted from said section image. The methods for extracting the brain midline characteristic regions may be similar to the methods for extracting the sagittal section characteristic regions aforementioned. For example, convolution may be performed on said section image using characteristic extraction operators. The section image processed by the convolution contains the extracted brain midline characteristic regions.

It should be understood that the "line" and the "brain midline" mentioned herein should not be ideally interpreted as theoretical lines, but regions having certain width and/or thickness.

The characteristics extraction operator may be designed based on the characteristics of the brain midline to be extracted. In the embodiments, the characteristics of the brain midline are similar to the characteristics of the median sagittal section described above. Therefore, the characteristic extractions operator which is similar to the characteristic extraction operator described above, such as similar to any one of the operators (1) to (5), may be used.

After the brain midline characteristic regions are extracted, at least two characteristic points which satisfy certain conditions may be selected from the brain midline characteristic regions, and characteristic point parameters of the at least two characteristic points may be recorded. The characteristic point parameters of the characteristic point may include the coordinates of the characteristic point and/or the value of the characteristic point (for example, the gray value or the result value of convolution) or other suitable parameters.

The certain conditions mentioned herein may be determined based on the properties of the characteristic extraction operator used. For example, when the operators similar to the characteristic extraction operators (1) to (5) above are used, the certain condition may be set as that the result value of convolution of the point is greater than a threshold. The threshold may be an empirical parameter and may be determined as required.

S41: detecting straight lines.

The selected characteristic points generally determine straight lines. In one embodiment, the straight line determined by the selected characteristic points may be acquired, which represents the brain midline in the section image.

The weight Hough transformation, the random Hough transformation and the stochastic optimal energy method described above may also be suitable for acquiring the straight lines in the present step after simple modification in details.

For example, the standard equation of a straight line may be $\rho=\cos\theta X+\sin\theta Y$, which has two parameters $\theta$ and $\rho$. Compared with the plane equation, there is no the parameter $\varphi$. When the weighted Hough transformation or the random Hough transformation is used, the Hough matrix is a two-dimensional $\rho\_\theta$ matrix. When the random Hough transformation or the stochastic optimal energy method is used, two points may be randomly selected from the selected characteristic points for each iteration, which may be enough to acquire a straight line. The other parts of the methods for acquiring the straight line may be substantially similar to the methods for acquiring the plane described above and will not be described in details herein.

In one embodiment, other methods may also be used to acquire the straight line determined by the selected characteristic points, for example, including, but not limited to, random transformation, phase encoding or least square estimation, etc.

Based on the characteristics of the median sagittal section image in the three-dimensional image of a fetal head, the brain midline straight lines acquired will determine a plane. This plane determined by the brain midline straight lines may be the plane on which the median sagittal section image is located.

Therefore, after the brain midline straight lines in the extracted section images are acquired in the step 111, the plane determined by the brain midline straight lines may be acquired in step 112. In this way, the plane on which the median sagittal section is located, i.e., the plane on which the median sagittal section image of the head of the fetus is located, may be acquired.

Various methods may be used to acquire the plane determined by the brain midline straight lines. For example, in some embodiments, three points which are not collinear may be selected from the acquired brain midline straight lines. The coordinates of the three points may be substituted into the plane equation to calculate the plane parameters. In other embodiments, these steps may be performed for several times and the average of the results of the acquisition will be the final acquisition result.

Another method may also be used. N points may be selected from the acquired brain midline straight lines and the plane parameters may be fitted using least square estimation. In other embodiments, the N points selected may serve as inputs and the plane parameters may be acquired using the Hough transformation, the random Hough transformation, the stochastic optimal energy method or the like which are similar to those described above.

After the median sagittal section image of the fetal head is extracted using the methods of the embodiments above, the orientation of the fetal head and/or the fetal face may be determined with reference to the embodiments above. Based on the determined orientation, the median sagittal section image in which the fetal head is upside down may be adjusted such that the head is upright and/or the orientation of the face may be marked in the median sagittal section image. Thereafter the adjusted and/or marked median sagittal section image may be displayed.

As described above and with further reference to FIG. 4, the tissue structures outside both sides of the median sagittal section in a fetal head are approximate symmetrical with respect to the median sagittal section, therefore the image data of the three-dimensional image of a fetal head outside both sides of the median sagittal section image will have approximate symmetry with respect to the median sagittal section image. In one embodiment, this characteristic may be used to acquire the median sagittal section image from the three-dimensional volume data. For example, a plurality of candidate section images may be selected from the three-dimensional volume data and the symmetry of the areas outside both sides of the candidate section images may be calculated. The candidate section image with best symmetry of areas outside both sides thereof may be the median sagittal section image desired.

Figure 23:
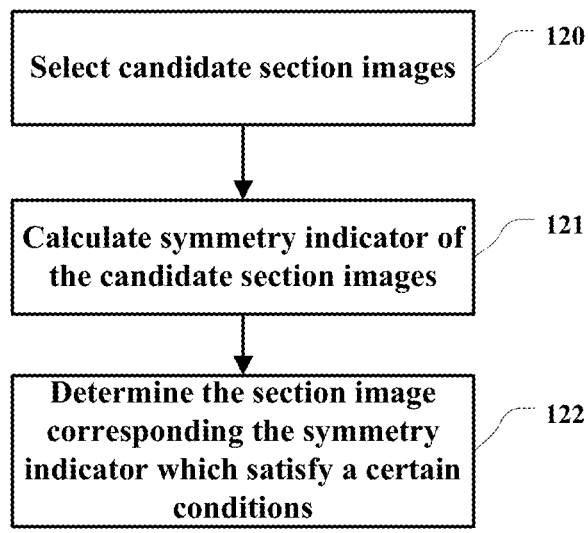
FIG. 23 is a flow chart for extracting the median sagittal section image in one embodiment.

For example, in one embodiment, a schematic flow chart of extracting the median sagittal section image from the three-dimensional volume data may be as shown in FIG. 23, which may include selecting candidate section image (step 120), calculating symmetry indicators of the candidate section images (step 121) and determining the section image corresponding to the symmetry indicator which satisfy a certain condition (step 122).

In step 120, a group of candidate section images may be selected from the three-dimensional volume data. The candidate section images may be selected as required. For example, in one embodiment, all section images in a certain range in the three-dimensional volume data which are a certain spacing (or step) apart from each other in one or more certain directions may be selected as the candidate section images. Herein, the "certain range" may be an angle range with respect to one or more lines and/or planes in the three-dimensional volume data. Alternatively, the "certain range" may also be a distance range with respect to one or more points, lines and/or planes in the three-dimensional volume data. The "in one or more certain directions" may mean that the normal line of the section image is in said one or more certain directions. The "spacing" or "step" may be a distance spacing or step, or a angle spacing or step.

In one embodiment, all section images which are certain spacing or step apart from each other in one or more certain directions in the whole of the three-dimensional volume data may be selected. Alternatively, in one embodiment, some prior knowledge may be used to assist the selection of the candidate section images to exclude the section images for which it is impossible to be the median sagittal section image. For example, since the median sagittal section of the head of the fetus is a longitudinal section (i.e., a section in the direction from the top to the neck of the fetus) which is located at the center position of the head of the fetus, the longitudinal section images which are located substantially at the center position of the head may be selected as the candidate section images based on the direction of the fetus image in the three-dimensional volume data. In the present disclosure, the section images in the direction from the top portion to the neck portion of the fetus in all, or at least a part, of the three-dimensional volume data (in other words, the section images which are substantially parallel to the direction from the top portion to the neck portion of the fetus, or the section images whose normal lines are substantially perpendicular to the direction from the top portion to the neck portion of the fetus) may be referred to as "longitudinal section image" of the three-dimensional volume data.

Therefore, in one embodiment, a group of longitudinal section images in the three-dimensional volume data may be selected as the candidate section images. For example, a group of longitudinal section images which are located at the center position of the head of the fetus (for example, all longitudinal section images which are a certain spacing or step apart from each other in a certain region at the center of the head) may be selected as the candidate section images.

Alternatively, in one embodiment, user inputs which indicate the possible range of the median sagittal section image may be received. Thereafter, the section images in the range indicated by the user may be selected as the candidate section images In one embodiment, all section images which are a certain step apart from each other in the whole of the three-dimensional volume data may be selected as the candidate section images. That is, all section images within the whole three-dimensional volume data may be searched using a certain step For example, in one embodiment, when the plane equation in the formula (6) is used, the candidate section images may be selected by determining the ranges of the plane parameters $\theta$, $\varphi$ and $\rho$ and the values of the steps $\theta$step, $\varphi$step and $\rho$step.

Similarly, when the plane equation aX+bY+cZ+d=0 Z=aX+bY+c or Y=aX+bZ+c is used, the candidate section images may be selected by determining the ranges of a, b, c and d and their steps.

For example, when all section images which are a certain step apart from each other in the whole of the three-dimensional volume data are selected as the candidate section images, the rang of $\rho$ may be as shown in the formula (7) and the largest ranges of $\theta$ and $\varphi$ may be, for example, $0°\leq\theta<360°$ and $-90°\leq\varphi\leq90°$ (with reference to FIG. 16). It will be understood that when the coordinate system is defined in different way the ranges of the parameters will be different.

The steps $\theta$step, $\varphi$step and $\rho$step may be determined based on the acquisition accuracy required and are not limited by the present disclosure. For example, in one embodiment, $\theta_{step}=1$, $\varphi_{step}=1$, $\rho_{step}=2$. It will be understood that the steps may also be other values based on the acquisition accuracy required.

After the candidate section images are selected, in step 121, a symmetry indicator may be calculated for each candidate section image ($\rho$, $\theta$, $\varphi$).

The symmetry indicator may be mainly used to measure the similarity of the data located outside both sides of the candidate section image.

For example, in one embodiment, for each candidate section image, at least one pair of first region and second region, which are located outside both sides of the candidate section image in the three-dimensional volume data, may be selected. The first region and the second region are symmetrical with respect to the candidate section image. Then the data in the first region and the data in the second region may be used to calculate the symmetry indicator of the candidate section image Herein, the "data in the first region" may refer to the values of the data points of the three-dimensional volume data which are located in the first region. Similarly, the "data in the second region" may refer to the values of the data points of the three-dimensional volume data which are located in the second region.

In one embodiment, for each candidate section image, a plurality of pairs of first region and second region may be selected. A symmetry indicator may be calculated for each pair of first region and second region. Therefore a plurality of symmetry indicators may be obtained. Thereafter, the symmetry indicator of the candidate section image may be obtained based on the plurality of symmetry indicators. For example, the symmetry indicator of the candidate section image may be the average of the plurality of symmetry indicators. Alternatively, the symmetry indicator of the candidate section image may be the weighted average of the plurality of symmetry indicators, where the weighted coefficients may be determined based on the location of the selected pair of first region and second region and other factors. In one embodiment, the final symmetry indicator of the candidate section image may be a function of the plurality of symmetry indicators.

The symmetry indicator may be calculated by various ways.

For example, in one embodiment, the symmetry indicator may be the sum of the absolute value of the difference between the gray values of the corresponding points in the first region and in the second region, i.e., $$E = \sum_{I_L, I_R \in \Omega} |I_L - I_R| \quad (12)$$

where E is the symmetry indicator, $\Omega$ is the first region and the second region, $I_L$ is the data value of the point in the first region, and $I_R$ is the data value of the point in the second region which is symmetrical with the point in the first region with respect to the candidate section image. The "corresponding points in the first region and in the second region" mentioned above may refer to the points in the first region and in the second region which are symmetrical with respect to the candidate section image.

In one embodiment, the symmetry indicator of the candidate section image may also be the correlation coefficient between the first region and the second region, i.e., $$E = \frac{\sum_{I_L, I_R \in \Omega} I_L I_R}{\sqrt{\sum_{I_L \in \Omega} I_L^2} \sqrt{\sum_{I_R \in \Omega} I_R^2}} \quad (13)$$

where E is the symmetry indicator, $\Omega$ is the first region and the second region, $I_L$ is the data value of the point in the first region, and $I_R$ is the data value of the point in the second region which is symmetrical with the point in the first region with respect to the candidate section image.

The symmetry indicator may be defined as described above, but not limited to. Other definitions may also be used. For example, the symmetry indicator may also be the Euclidean distance between the first region and the second region, the cosine similarity between the first region and the second region, or the like.

The symmetry indicators may be calculated for all candidate section images and thus a group of symmetry indicators may be obtained. Thereafter, a characteristic symmetry indicator which satisfies characteristic conditions may be selected from the group of symmetry indicators. In one embodiment, the candidate section image corresponding to the characteristic symmetry indicator is the desired median sagittal section image of the fetal head.

The "characteristic conditions" herein may be conditions which indicate the optimal symmetry of the candidate section image. The characteristic conditions may be determined based on the ways for calculating the symmetry indicators. For example, for the symmetry indicator calculated using the formula (12), the smaller the E (i.e. the symmetry indicator), the more similar the image pixels outside both sides of the candidate section image, i.e., the better the symmetry. Therefore, in this case, the characteristic condition may be that "the symmetry indicator is the smallest". While for the symmetry indicator calculated using the formula (13), the larger the E (i.e., the similarity indicator) (for the formula (13), the closer to 1 the E), the more similar the image pixels outside both sides of the candidate section image, i.e., the better the symmetry. Therefore, in this case, the characteristic condition may be that "the symmetry indicator is the closest to 1" or "the symmetry indicator is the largest".

When the symmetry indicators are calculated in other ways, the characteristic conditions may be accordingly defined. For example, when the symmetry indicator is the Euclidean distance between the first region and the second region, the characteristic condition may be that "the symmetry indicator is the smallest". That is, in this case, the smaller the symmetry indicator (i.e., the smaller the Euclidean distance), the better the symmetry of the first region with the second region. When the symmetry indicator is the cosine similarity between the first region and the second region, the characteristic condition may be that "the symmetry indicator is the largest". That is, the larger the symmetry indicator (i.e., the larger the cosine similarity), the better the symmetry of the first region with the second region.

After the median sagittal section image of the fetal head is extracted using the methods of the embodiments above, the orientation of the fetal head and/or the fetal face may be determined with reference to the embodiments above. Based on the determined orientation, the median sagittal section image in which the fetal head is upside down may be adjusted such that the head is upright and/or the orientation of the face may be marked in the median sagittal section image. Thereafter the adjusted and/or marked median sagittal section image may be displayed.

As described above, some special structures will be shown in the median sagittal section image of a fetal head. In other words, the median sagittal section image of a fetal head will contain some special structural features. In one embodiment, this characteristic of the median sagittal section image of a fetal head may be used. A template image (or standard reference image) of the median sagittal section image of a fetal head may be generated using the median sagittal section images of fetal heads which have been obtained previously. Thereafter, in the three-dimensional imaging process, the section images of the obtained three-dimensional volume data may be matched with the template image and the similarity between the section images of the three-dimensional volume data and the template image may be calculated. The section image in the three-dimensional volume data with largest similarity with the template image may be the median sagittal section image of the head of the fetus.

Figure 24:
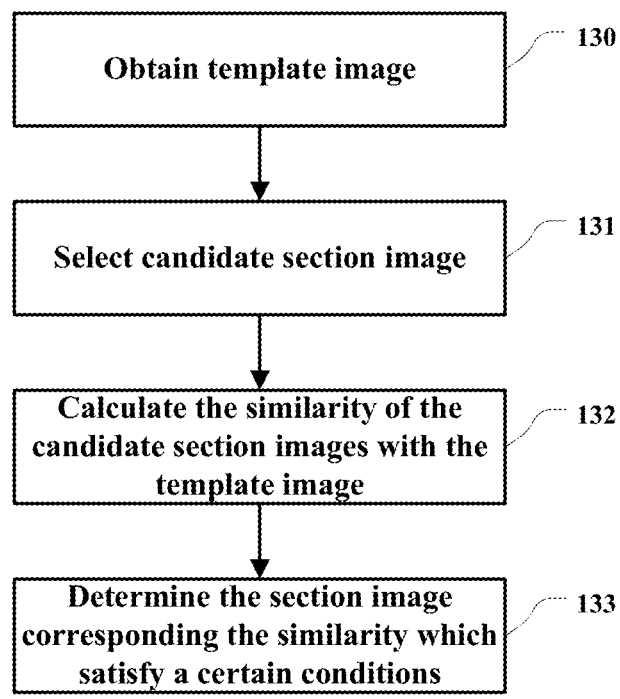
FIG. 24 is a flow chart for extracting the median sagittal section image in one embodiment.

For example, in one embodiment, a schematic flow chart of extracting the median sagittal section image from the three-dimensional volume data may be as shown in FIG. 24, which may include obtaining a template image (step 130), selecting candidate section images (step 131), calculating a similarity indicator of each candidate section image with the template image (step 132) and determining a section image corresponding to the similarity indicator which satisfy a certain condition (step 133).

In step 130, a template image of the median sagittal section image of a fetal head may be obtained. In one embodiment, the template image may be generated based on the median sagittal section images of the heads of other fetuses which have been obtained previously, and may be stored in a memory. In the three-dimensional imaging process, the template image may be read from the memory. Alternatively, the template image may also be generated in the three-dimensional imaging process.

The template image may be one or more. For example, a plurality of template images may be used to match the section images of three-dimensional volume data with different sizes.

In the case that a plurality of template images are used, each candidate section image may be matched with each template image.

After the template images are obtained, a group of candidate section images may be selected from the three-dimensional volume data in step 131. The candidate section images may be selected as required. For example, in one embodiment, all section images in a certain range in the three-dimensional volume data which are a certain spacing (or step) apart from each other in one or more certain directions may be selected as the candidate section images. Herein, the "certain range" may be a angle range with respect to one or more lines and/or planes in the three-dimensional volume data, or be a distance range with respect to one or more points, lines and/or planes in the three-dimensional volume data; the "in one or more certain directions" may mean that the normal line of the section image is in said one or more certain directions; the "spacing" or "step" may be a distance spacing or step, or a angle spacing or step.

In one embodiment, all section images which are certain spacing or step apart from each other in one or more certain directions in the whole of the three-dimensional volume data may be selected. In one embodiment, some prior knowledge may be used to assist the selection of the candidate section images to exclude the section images for which it is impossible to be the median sagittal section image. For example, since the median sagittal section of a fetal head is a longitudinal section (i.e., a section in the direction from the top to the neck of the fetus) which is located at the center position of the fetal head, the longitudinal section images which are located substantially at the center position of the head may be selected as the candidate section images roughly based on the direction of the fetus image in the three-dimensional volume data. For example, a group of longitudinal section images which are located at the center position of the head of the fetus (for example, all longitudinal section images which are a certain spacing or step apart from each other within a certain region at the center of the head) may be selected as the candidate section images.

Alternatively, in one embodiment, user inputs which indicate the possible range of the median sagittal section image may be received. Thereafter, the section images in the range indicated by the user may be selected as the candidate section images.

In one embodiment, all section images which are a certain step apart from each other in the whole of the three-dimensional volume data may be selected as the candidate section images. That is, all section images in the whole three-dimensional volume data may be matched with the template image with a certain step.

For example, in one embodiment, when the plane equation in the formula (6) is used, the candidate section images may be selected by determining the ranges of the plane parameters θ, φ and ρ and the values of the steps θstep, φstep and ρstep.

Similarly, when the plane equation aX+bY+cZ+d=0, Z=aX+bY+c or Y=aX+bZ+c is used, the candidate section images may be selected by determining the ranges of a, b, c and d and their steps.

For example, when all section images which are a certain step apart from each other in the whole of the three-dimensional volume data are selected as the candidate section images, the rang of ρ may be as shown in the formula (7) and the largest ranges of θ and φ may be, for example, $0° \leq \theta < 360°$ and $-90° \leq \varphi \leq 90°$ (with reference to FIG. 16). It will be understood that when the coordinate system is defined in different way the ranges of the parameters will be different.

The steps θstep, φstep and ρstep may be determined based on the acquisition accuracy required and are not limited by the present disclosure. For example, in one embodiment, $\theta_{step}=1$, $\varphi_{step}=1$, $\rho_{step}=2$. It will be understood that the steps may also be other values based on the acquisition accuracy required.

As described above, in one embodiment, only one template image is used. In this case, the template image may be generated in a certain size. Before the candidate section images are selected from the three-dimensional volume data, the methods may further include a step of adjusting the three-dimensional volume data or the template image. In this step, the three-dimensional volume data and the template image may be adjusted to a same scale space. In other words, the sizes of the corresponding structures in the three-dimensional volume data and in the template image are made to be approximately the same. By this adjustment, the corresponding structures in the three-dimensional volume data and in the template image have approximately same sizes. Thereby, the match is easier to be realized, the match effect is better and the calculation of the match is reduced.

When adjusting the three-dimensional volume data or the template image, special structural features (for example, the skull ring, etc.) in a section image (for example, the most middle frame of image, i.e., the F/2-th frame of image, or the frame of image near the most middle frame or other frame of image, or other section image) in the three-dimensional volume data may be detected, and then the three-dimensional volume data may be converted into the same scale with the template image by rotation, translation and/or zooming based on the size of the detected structural features.

Herein, converting the three-dimensional volume data into the same scale with the template image may refer to making the same or corresponding structural features in the three-dimensional volume data and in the template image to have same size by conversion.

Herein, the "same" may refer to that they are substantially the same or similar, but not be strictly limited to be exactly the same. Rather, there may be a certain difference. In other words, the "same" herein should not be strictly interpreted.

In the embodiments, any other suitable method may also be used to adjusting the three-dimensional volume data and the template image to the same scale space.

After the candidate section images are selected, each of the candidate section images may be matched with the template image in step 132. For example, a similarity indicator of each candidate section image with the template image may be calculated.

The similarity indicator may be used to measure the similarity of the candidate section image with the template image. In the embodiments, the similarity indicator may be calculated using a variety of ways.

For example, in some embodiments, the similarity indicator may be the sum of the absolute value of the difference between the gray values of the corresponding points in the candidate section image and in the template image. I.e., $$E = \sum_{I_L, I_R \in \Omega} |I_L - I_R| \qquad (14)$$

where E is the similarity indicator, $\Omega$ is image space of the candidate section image, $I_L$ is the data value of the point in the candidate section image, and $I_R$ is the data value of the point in the template image corresponding to the point in the candidate section image. Herein, the "corresponding points in the candidate section image and in the template image" mentioned above may refer to the points in the candidate section image and in the template image which have same location.

In one embodiment, the similarity indicator may also be the correlation coefficient between the candidate section image and the template image, i.e., $$E = \frac{\sum_{I_L, I_R \in \Omega} I_L I_R}{\sqrt{\sum_{I_L \in \Omega} I_L^2} \sqrt{\sum_{I_R \in \Omega} I_R^2}} \qquad (15)$$

where E is the similarity indicator, $\Omega$ is the image space of the candidate section image, $I_L$ is the data value of the point in the candidate section image, and $I_R$ is the data value of the point in the template image corresponding to the point in the candidate section image.

The similarity indicator may be defined as described above, but not limited to. Other definition may also be used.

The similarity indicators of all candidate section images may be calculated and thus a group of similarity indicators may be obtained. Thereafter, a characteristic similarity indicator which satisfies characteristic conditions may be selected from the group of similarity indicators. In the embodiments, the candidate section image corresponding to the characteristic similarity indicator may be the desired median sagittal section image of the head of the fetus.

The "characteristic conditions" herein may be conditions which indicate the best similarity of the candidate section image with the template image. The characteristic conditions may be determined based on the ways for calculating the similarity indicators.

For example, for the similarity indicator calculated using the formula (14), the smaller the E (i.e. the similarity indicator), the more similar the candidate section image with the template image, i.e., the better the similarity. Therefore, in this case, the characteristic condition may be that "the similarity indicator is the smallest".

While for the similarity indicator calculated using the formula (15), the larger the E (i.e., the similarity indicator) (for the formula (15), the closer to 1 the E), the more similar the candidate section image with the template image, i.e., the better the similarity. Therefore, in this case, the characteristic condition may be that "the similarity indicator is the closest to 1" or "the similarity indicator is the largest".

When the similarity indicators are calculated in other ways, the characteristic conditions may be defined accordingly. For example, when the similarity indicator is the Euclidean distance between the candidate section image and the template image, the characteristic condition may be that "the similarity indicator is the smallest". That is, in this case, the smaller the similarity indicator (i.e., the smaller the Euclidean distance), the better the similarity of the candidate section image with the template image. When the similarity indicator is the cosine similarity between the candidate section image and the template image, the characteristic condition may be that "the similarity indicator is the largest". That is, the larger the similarity indicator (i.e., the larger the cosine similarity), the better the similarity of the candidate section image with the template image.

In some embodiments, after the median sagittal section image of the fetal head is extracted and the orientation of the fetal head (e.g., the orientation of the top of the head and/or the face) is determined, the median sagittal section image may be adjusted to desired orientation and/or the orientation of the fetal head may be marked on the median sagittal section image. Thereafter, the adjusted or marked median sagittal section image may be displayed on the display.

In some embodiments, the methods for extracting the median sagittal section image of the fetal head will not be limited to those described above. Any other suitable methods for extracting the median sagittal section image of the fetal head may also be used.

In some embodiments, the terms such as "top", "down", "front", "rear", "left" and "right", etc. have been used, where "top" and "down" may be defined respectively as the orientations where the head in the image is upright and upside down according to the human observation habits, "front" and "rear" may be defined respectively as the orientations corresponding to the fetal face and the fetal back according to the human observation habits, and "left" and "right" may be relative. "Left" may correspond to "front". Alternatively, "left" may correspond to "rear". However, the present disclosure will not be limited thereto.

The person skilled in the art will understand that all or a part of the steps of the methods in the embodiments above may be implemented by instructing related hardware, such as a processor, to execute programs stored in a non-transitory computer readable storage medium. The computer readable storage medium may include read-only memory, random access memory, disk or disc, etc.

The present disclosure has been described in detail with reference to specific embodiments. However, the implementation of the present disclosure will not be limited thereto. Many substitutions and modifications may be made by the person ordinarily skilled in the art to which the present disclosure belongs without departing from the concepts of the present disclosure.

We claim:

1. A three-dimensional ultrasound imaging method, comprising:

transmitting ultrasound waves to a fetal head;

receiving ultrasound echoes to obtain ultrasound echo signals;

obtaining a three-dimensional volume data of the fetal head according to the ultrasound echo signals;

extracting a median sagittal section image from the three-dimensional volume data based on characteristics of a median sagittal section of a fetal head;

detecting image regions representing specific tissue areas of the fetal head in at least one of the extracted median sagittal section image and a section image which is parallel to or intersects with the extracted median sagittal section image;

determining an orientation of the fetal head in the at least one of the extracted median sagittal section image and the section image which is parallel to or intersects with the extracted median sagittal section image based on the image regions; and rotating the extracted median sagittal section image based on the orientation of the fetal head such that in the rotated and extracted median sagittal section image the fetal head is in a pre-set orientation, or marking the orientation of the fetal head in the extracted median sagittal section image.

2. The method of claim 1, wherein detecting the image regions representing specific tissue areas of the fetal head in at least one of the extracted median sagittal section image and the section image which is parallel to or intersects with the extracted median sagittal section image and determining the orientation of the fetal head based on the image regions comprises:

detecting at least two image regions representing at least two specific tissue areas of the fetal head which have certain mutual positional relationship in at least one of the extracted median sagittal section image and the section image which is parallel to or intersects with the extracted median sagittal section image, and determining the orientation of the fetal head based on the mutual positional relationship between the at least two image regions.

3. The method of claim 1, wherein detecting the image regions representing specific tissue areas of the fetal head in at least one of the extracted median sagittal section image and the section image which is parallel to or intersects with the extracted median sagittal section image and determining the orientation of the fetal head based on the image regions comprises:

detecting an image region representing a specific tissue region in the fetal head which has directional characteristics in at least one of the extracted median sagittal section image and the section image which is parallel to or intersects with the extracted median sagittal section image, and determining the orientation of the fetal head based on at least one of a position and a shape of the image region.

4. The method of claim 3, wherein the image region is a region representing a skull of the fetal head, and wherein detecting an image region representing the specific tissue region in the fetal head which has directional characteristics in at least one of the extracted median sagittal section image and the section image which is parallel to or intersects with the extracted median sagittal section image and determining the orientation of the fetal head based on the image region comprises:

selecting at least one of the extracted median sagittal section image and at least one section image parallel to the extracted median sagittal section image and extracting characteristics regions corresponding to the skull from the selected section image based on characteristics of the skull in ultrasound image to obtain candidate regions representing the skull;

determining an orientation of the skull based on the candidate regions; and determining the orientation of the fetal head based on the orientation of the skull.

5. The method of claim 4, wherein:

extracting the characteristics regions corresponding to the skull comprises extracting regions whose grayscale values are greater than a pre-set threshold in the selected section image as the characteristics regions, or designing operators based on differential, calculating a convolution of the operators with the selected section image and selecting regions whose convolution values are greater than a pre-set threshold as the characteristics regions;

obtaining the candidate regions representing the skull comprises selecting at least one characteristics region of which a sum of characteristics values are maximum as the candidate regions, or selecting at least one characteristics region of which average characteristics values are maximum as the candidate regions, or extracting characteristics from the characteristics regions, inputting the extracted characteristics into a pre-trained classifier and determining the candidate regions based on classification results; and determining the orientation of the skull comprises determining the orientation of the skull based on bending direction of the skull.

6. The method of claim 3, wherein the image region is a region representing a cavum septi pellucid of the fetal head, and wherein detecting an image region representing the specific tissue region in the fetal head which has directional characteristics in at least one of the extracted median sagittal section image and the section image which is parallel to or intersects with the extracted median sagittal section image and determining the orientation of the fetal head based on the image region comprises:

detecting a connected region corresponding to the cavum septi pellucid from the extracted median sagittal section image based on characteristics of the cavum septi pellucid in ultrasound image;

determining an orientation of the cavum septi pellucid based on the connected region; and determining the orientation of the fetal head based on the orientation of the cavum septi pellucid.

7. The method of claim 6, wherein detecting the connected region corresponding to the cavum septi pellucid from the extracted median sagittal section image comprises segmenting the extracted median sagittal section image to obtain at least one region and selecting a region which is most similar to the cavum septi pellucid from the at least one region based on characteristics of the at least one region as the connected region corresponding to the cavum septi pellucid.

8. The method of claim 3, wherein the image region is a region representing a cavum septi pellucid of the fetal head, and wherein detecting an image region representing the specific tissue region in the fetal head which has directional characteristics in at least one of the extracted median sagittal section image and the section image which is parallel to or intersects with the extracted median sagittal section image and determining the orientation of the fetal head based on the image region comprises:

detecting a cavum septi pellucid region from the extracted median sagittal section image based on characteristics of the cavum septi pellucid in ultrasound image;

selecting at least one frame of horizontal section image form the three-dimensional volume data, performing an ellipsoid or ellipse detection on the horizontal section image and obtaining a center of the detected ellipse or ellipsoid; and comparing a coordinate of the cavum septi pellucid region and a coordinate of the center and determining the orientation of the fetal head based on the comparison.

9. The method of claim 8, wherein detecting the cavum septi pellucid region from the extracted median sagittal section image comprises:

segmenting the extracted median sagittal section image to obtain at least one region and selecting a region which is most similar to the cavum septi pellucid from the at least one region based on characteristics of the at least one region as the cavum septi pellucid region; and performing the ellipsoid or ellipse detection on the horizontal section image comprises designing operators based on differential, extracting characteristics of the horizontal section image using the operators and performing the ellipsoid or ellipse detection on the extracted characteristics.

10. A three-dimensional ultrasound imaging device, comprising:

a probe which transmits ultrasound waves to a fetal head and receives ultrasound echoes to obtain ultrasound echo signals;

a three-dimensional imaging unit which obtains a three-dimensional volume data of the fetal head using the ultrasound echo signals, extracts a median sagittal section image from the three-dimensional volume data based on characteristics of a median sagittal section of a fetal head, determines an orientation of the fetal head in the at least one of the extracted median sagittal section image and the section image which is parallel to or intersects with the extracted median sagittal section image based on the image regions, and rotates the extracted median sagittal section image based on the orientation of the fetal head such that in the rotated and extracted median sagittal section image the fetal head is in a pre-set orientation or marks the orientation of the fetal head in the extracted median sagittal section image; and a display which displays the extracted median sagittal section image.

11. The device of claim 10, wherein the three-dimensional imaging unit further detects at least two image regions representing at least two specific tissue areas of the fetal head which have certain mutual positional relationship in at least one of the extracted median sagittal section image and the section image which is parallel to or intersects with the extracted median sagittal section image, and determining the orientation of the fetal head based on the mutual positional relationship between the at least two image regions.

12. The device of claim 10, wherein the three-dimensional imaging unit further detects an image region representing a specific tissue region in the fetal head which has directional characteristics in at least one of the extracted median sagittal section image and a section image which is parallel to or intersects with the extracted median sagittal section image, and determining the orientation of the fetal head based on at least one of a position and a shape of the image region.

13. A three-dimensional ultrasound imaging method, comprising:

transmitting ultrasound waves to a fetal head;

receiving ultrasound echoes to obtain ultrasound echo signals;

obtaining a three-dimensional volume data of the fetal head according to the ultrasound echo signals;

extracting a median sagittal section image from the three-dimensional volume data based on characteristics of a median sagittal section of a fetal head;

detecting image regions representing specific tissue areas of the fetal head in at least one of the extracted median sagittal section image and a section image which is parallel to or intersects with the extracted median sagittal section image; and determining an orientation of the fetal head in the at least one of the extracted median sagittal section image and the section image which is parallel to or intersects with the extracted median sagittal section image based on the image regions.

* * * * *